(12) United States Patent
Uzawa et al.

(10) Patent No.: US 9,459,443 B2
(45) Date of Patent: Oct. 4, 2016

(54) ENDOSCOPIC OBJECTIVE OPTICAL SYSTEM AND IMAGING APPARATUS

(71) Applicant: OLYMPUS CORPORATION, Tokyo (JP)

(72) Inventors: Tsutomu Uzawa, Tokyo (JP); Masahiro Katakura, Tokyo (JP)

(73) Assignee: Olympus Corporation, Tokyo (JP)

( * ) Notice: Subject to any disclaimer, the term of this patent is extended or adjusted under 35 U.S.C. 154(b) by 64 days.

(21) Appl. No.: 14/309,539

(22) Filed: Jun. 19, 2014

(65) Prior Publication Data

US 2015/0042773 A1 Feb. 12, 2015

Related U.S. Application Data

(63) Continuation of application No. PCT/JP2013/085015, filed on Dec. 26, 2013.

(30) Foreign Application Priority Data

Feb. 22, 2013 (JP) .................................. 2013-033440

(51) Int. Cl.
| | |
|---|---|
| G02B 23/24 | (2006.01) |
| G02B 27/10 | (2006.01) |
| G02B 13/04 | (2006.01) |
| A61B 1/00 | (2006.01) |

(52) U.S. Cl.
CPC ......... *G02B 23/243* (2013.01); *A61B 1/00096* (2013.01); *A61B 1/00188* (2013.01); *G02B 13/04* (2013.01); *G02B 23/2446* (2013.01); *G02B 27/1066* (2013.01)

(58) Field of Classification Search
CPC .................................................. G02B 23/243
See application file for complete search history.

(56) References Cited

U.S. PATENT DOCUMENTS

| | | | | |
|---|---|---|---|---|
| 8,243,129 B2* | 8/2012 | Uzawa | ............... | A61B 1/00096 348/65 |
| 2003/0197802 A1* | 10/2003 | Kato | .................... | G02B 13/004 348/335 |
| 2004/0120031 A1* | 6/2004 | Fukaya | .............. | G02B 21/0012 359/375 |

(Continued)

FOREIGN PATENT DOCUMENTS

| | | |
|---|---|---|
| JP | 2000089105 A | 3/2000 |
| JP | 2008107391 A | 5/2008 |

(Continued)

*Primary Examiner* — Jay Au Patel
*Assistant Examiner* — Irfan Habib
(74) *Attorney, Agent, or Firm* — Kenyon & Kenyon LLP

(57) ABSTRACT

To allow placement of optical members by providing a long back focus, make aberrations less subject to manufacturing errors, and reduce variations in aberrations during focusing. An endoscopic objective optical system includes, in order from an object side, a front group with negative refractive power, a focusing lens, and a rear group with positive refractive power, wherein: the endoscopic objective optical system satisfies conditional expressions (1) to (4) below:

$$4 < FB/FL \tag{1}$$

$$FL/|fc| < 0.1 \tag{2}$$

$$-3 < F\_F/FL < -0.9 \tag{3}$$

$$2.5 < F\_R/FL < 5 \tag{4}$$

where FB is back focus of the entire system, FL is a focal length of the entire system, fc is a focal length of the focusing lens, $|fc|$ is an absolute value of fc, F_F is a focal length of the front group, and F_R is a focal length of the rear group.

4 Claims, 35 Drawing Sheets

(56) References Cited

U.S. PATENT DOCUMENTS

| | | | | |
|---|---|---|---|---|
| 2006/0083505 A1* | 4/2006 | Kashiwaba | ............... | G02B 7/10 396/79 |
| 2007/0091456 A1* | 4/2007 | Yamamoto | ........... | G02B 15/177 359/680 |
| 2010/0046093 A1* | 2/2010 | Takato | ................. | G02B 23/243 359/738 |
| 2010/0142058 A1* | 6/2010 | Takato | ................. | G02B 23/243 359/661 |
| 2011/0211267 A1* | 9/2011 | Takato | ............... | A61B 1/00188 359/784 |
| 2012/0057251 A1* | 3/2012 | Takato | ................. | G02B 23/243 359/749 |

FOREIGN PATENT DOCUMENTS

| | | |
|---|---|---|
| JP | 2008224842 A1 | 9/2008 |
| JP | 4675348 B2 | 2/2011 |
| JP | 4819969 B2 | 11/2011 |
| JP | 4919419 B2 | 4/2012 |
| WO | 2011070930 A1 | 6/2011 |
| WO | 2013027459 A1 | 2/2013 |

* cited by examiner

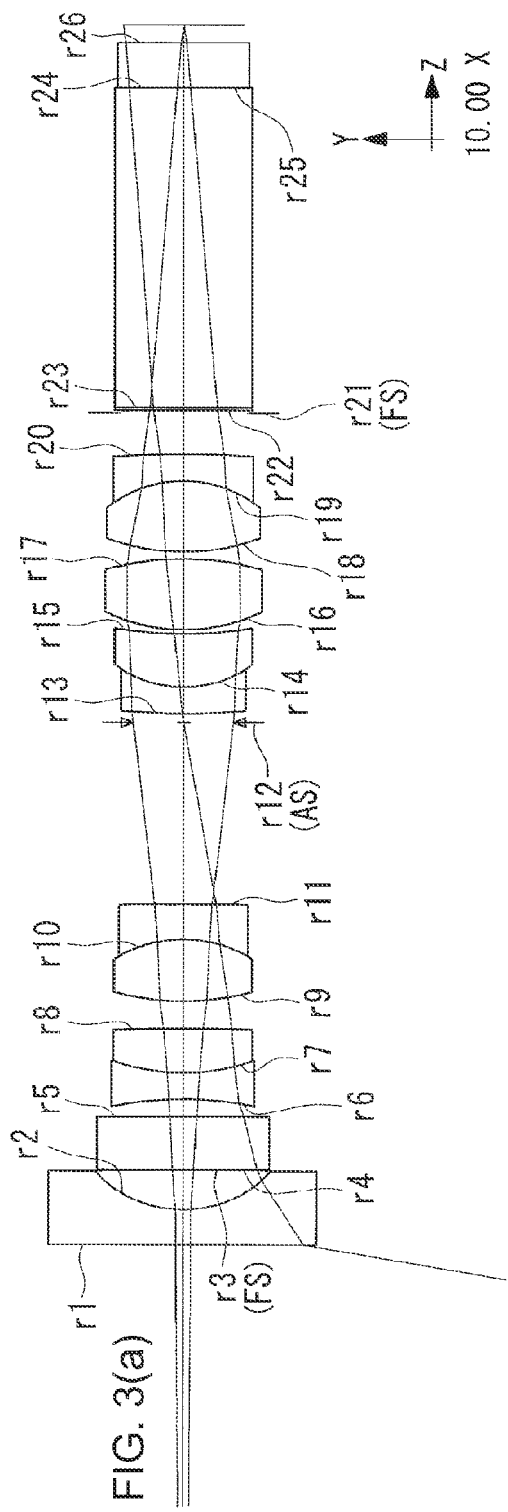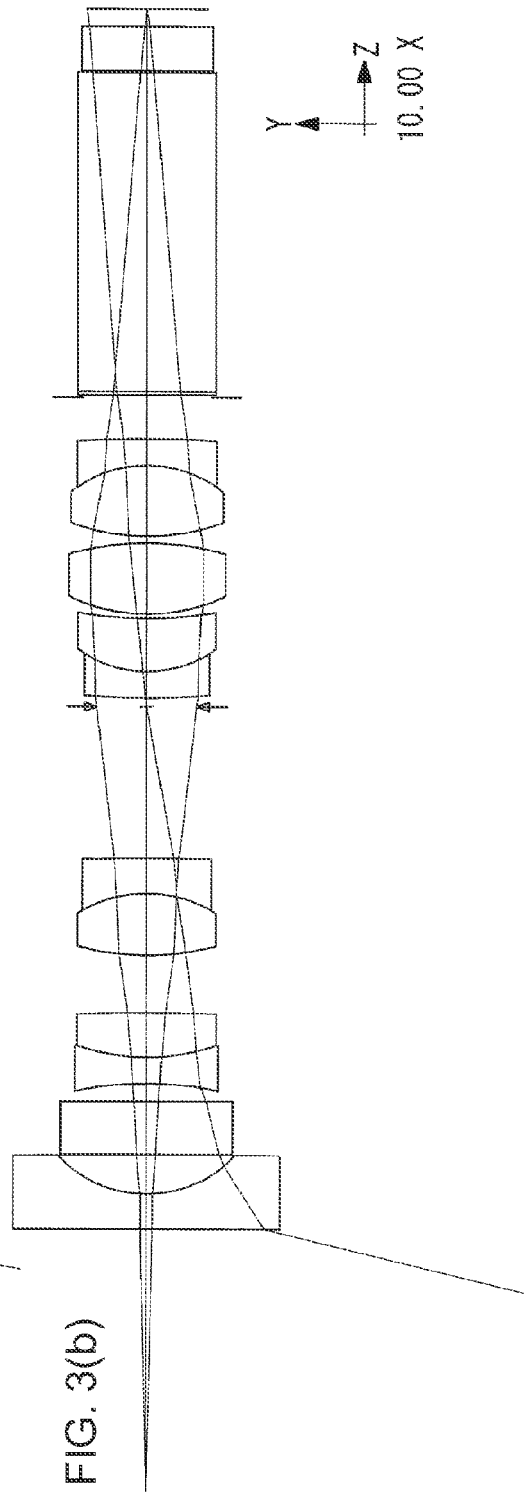

ENDOSCOPIC OBJECTIVE OPTICAL SYSTEM AND IMAGING APPARATUS

CROSS-REFERENCE TO RELATED APPLICATIONS

This application is a Continuation Application of International Application PCT/JP2013/085015 filed on Dec. 16, 2013, which claims priority to Japanese Application No. 2013-033440 filed on Feb. 22, 2013.
The Contents of International Application PCT/JP2013/085015 and Japanese application No. 2013-033440 are hereby incorporated by reference herein in its entirety.

TECHNICAL FIELD

The present invention relates to an endoscopic objective optical system, and more particularly, to an endoscopic objective optical system with a long back focus.

BACKGROUND ART

In an endoscopic objective optical system, it is sometimes necessary to provide a long back focus in order to place optical members such as a prism in an optical path. Objective optical lenses provided with such a long back focus are proposed, for example, in Patent Literatures 1 and 2.

According to both Patent Literatures 1 and 2, an optical member is placed between an objective lens and image plane. In particular, an optical path folding prism is placed according to Patent Literature 1 and an optical element is placed as a spectral optical member according to Patent Literature 2.

Also, in recent years, there has been a tendency for depth of field to become shallower due to increases in image quality of imaging devices. For example, Patent Literature 3 proposes an endoscopic objective lens equipped with a focusing function which, in order to ensure large imaging depth, keeps focal position constant by correcting shifts in the focal position caused by changes in working distance (WD).

On the other hand, as a result of increases in the image quality of imaging devices, it has become increasingly important to keep aberration variations at a low level during focusing in addition to adjusting focus along with variation in the working distance even in the case of an endoscopic objective optical system equipped with a focusing function.

CITATION LIST

Patent Literature

{PTL 1} The Publication of Japanese Patent No. 4919419
{PTL 2} The Publication of Japanese Patent No. 4675348
{PTL 3} The Publication of Japanese Patent No. 4819969

SUMMARY OF INVENTION

Technical Problem

However, according to the patent literatures described above, the aberration variations during focusing cannot be kept within a desired range because the back focus is not sufficiently long or because a focusing function is not provided or even if provided, it is not assumed that optical elements such as a prism will be placed in the optical path.

Also, as described above, it has become increasingly important to keep aberration variations at a low level during focusing. On the other hand, it is necessary to provide some play in order to improve slidability of a focusing lens, and consequently decentering of the focusing lens due to manufacturing errors is unavoidable. The manufacturing errors such as the decentering of the focusing lens make deterioration of aberrations conspicuous.

The present invention has been made in view of the above circumstances, and has an object to provide an endoscopic objective optical system which has a long back focus, allows placement of optical members such as a polarizing prism, makes aberrations less subject to manufacturing errors, and reduces variations in aberrations during focusing.

Solution to Problem

To achieve the above object, the present invention provides the following solutions.

One aspect of the present invention provides an endoscopic objective optical system comprising, in order from an object side to an image side, a front group provided with negative refractive power, a focusing lens, and a rear group provided with positive refractive power, wherein: the front group and the rear group are always fixed on an optical axis; and the endoscopic objective optical system satisfies conditional expressions (1) to (4) below:

$$4 < FB/FL \quad (1)$$

$$FL/|fc| < 0.1 \quad (2)$$

$$-3 < F\_F/FL < -0.9 \quad (3)$$

$$2.5 < F\_R/FL < 5 \quad (4)$$

where FB is back focus of the entire endoscopic objective optical system, the back focus being a distance from a lens surface of the rear group closest to the image side to a back focus position of the entire system, FL is a focal length of the entire endoscopic objective optical system, fc is a focal length of the focusing lens, |fc| is an absolute value of fc, F_F is a focal length of the front group, and F_R is a focal length of the rear group.

By satisfying the above conditional expressions, the present aspect reduces variations in aberrations due to manufacturing errors and variations in aberrations due to focusing by prescribing the focal length of the focusing lens while allowing placement of optical members such as a polarizing prism. Specifically, the present aspect makes it possible to suppress aberrations due to manufacturing errors, decrease influence on deterioration of optical performance, and, for example, reduce side blur. Also, the present aspect makes it possible to suppress variations in aberrations due to focusing, decrease variations in astigmatic aberrations, and prevent an image surface from becoming liable to incline to a negative side on a side of shorter working distance. Note that the focusing lens has positive or negative weak refractive power.

Also, the present aspect makes it possible to decrease influence of eccentricity errors on deterioration of optical performance while maintaining sufficient refractive power of the front group so as to be advantageous for a wider angle of view and reducing high order off-axis aberrations.

Furthermore, the present aspect makes it possible to keep lens size in a desired range while maintaining refractive power of the rear group and ensuring back focus.

In the aspect described above, preferably the focusing lens has a positive refractive index; and focus is set to a side of shorter working distance by moving the focusing lens to an image side when the working distance changes from a longer side to the shorter side.

This makes it possible to set focus to the side of shorter working distance by moving the focusing lens to the image side on the optical axis.

BRIEF DESCRIPTION OF DRAWINGS

FIGS. 3(a) and 3(b) are sectional views showing the overall configuration of the objective optical system according to Example 1 of the present invention, where FIG. 3(a) shows a normal observation mode and FIG. 3(b) shows a short distance observation mode.

FIG. 7(a) shows a normal observation mode and FIG. 7(b) shows a short distance observation mode.

FIG. 11(a) shows a normal observation mode and FIG. 11(b) shows a short distance observation mode.

FIG. 15(a) shows a normal observation mode and FIG. 15(b) shows an short distance observation mode.

FIG. 18(a) shows a normal observation mode and FIG. 18(b) shows a short distance observation mode.

FIG. 22(a) shows a normal observation mode and FIG. 22(b) shows a short distance observation mode.

FIG. 26(a) shows a normal observation mode and FIG. 26(b) shows a short distance observation mode.

FIG. 30(a) shows a normal observation mode and FIG. 30(b) shows a short distance observation mode.

FIG. 33(a) is a diagram schematically showing an overall configuration and FIG. 33(b) is a diagram showing orientations of subjects in images formed, respectively, in a first and second regions of an imaging device.

FIG. 35(a) shows an example and FIG. 35(b) shows another example.

DESCRIPTION OF EMBODIMENTS

First Embodiment

An objective optical system according to a first embodiment of the present invention will be described below with reference to the drawings.

Figure 1:
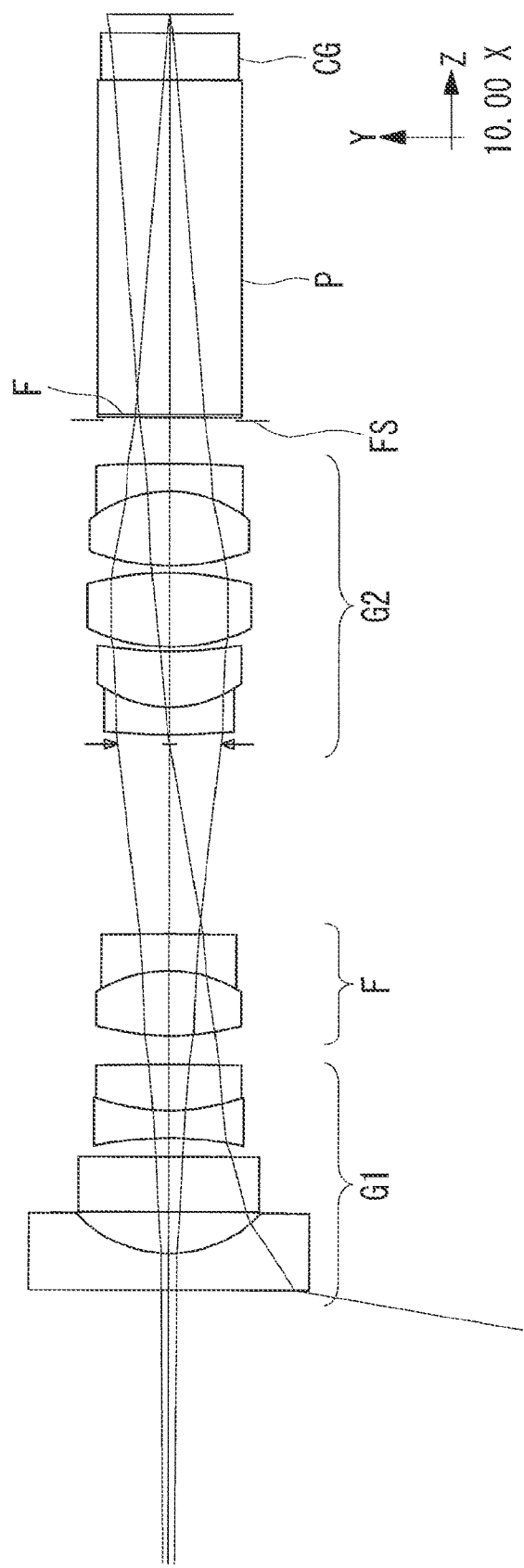
FIG. 1 is a sectional view showing an overall configuration of an objective optical system according to a first embodiment of the present invention.

FIG. 1 is a sectional view showing an overall configuration of the endoscopic objective optical system 1 according to the present embodiment. As shown in FIG. 1, the endoscopic objective optical system 1 includes, in order from an object side, a front group G1 provided with negative refractive power (hereinafter referred to simply as "negative"), a focusing lens F, and a rear group G2 provided with positive refractive power (hereinafter referred to simply as "positive").

An optical filter F, an optical prism P, and an optical member CG such as cover glass are placed on an image side of the positive rear group G2, where the cover glass is adapted to seal an imaging device (not shown).

The imaging device is placed near an image surface of the endoscopic objective optical system, making up the endoscopic objective optical system and an imaging optical system.

The endoscopic objective optical system, in which the front group and rear group are always fixed on an optical axis, is configured to satisfy the following conditional expressions:

$$4 < FB/FL \quad (1)$$

$$FL/|fc| < 0.1 \quad (2)$$

where FB is back focus of the entire endoscopic objective optical system, the back focus being a distance from a lens surface of the rear group closest to the image side to a back focus position of the entire system, FL is a focal length of the entire endoscopic objective optical system, fc is a focal length of the focusing lens, and |fc| is an absolute value of fc.

Conditional expression (1) prescribes the back focus. When the back focus is smaller than 4, i.e., the lower limit of conditional expression (1), it becomes difficult to place optical members such as a polarizing prism.

Conditional expression (2) concerns variations in aberrations due to manufacturing errors and variations in aberrations due to focusing and prescribes the focal length of the focusing lens. The focusing lens has positive or negative weak refractive power. When 0.1, i.e., the upper limit of conditional expression (2), is exceeded, influence of eccentricity errors on deterioration of optical performance increases, which is not desirable. Specifically, even if eccentricity errors remain the same, side blur and the like are liable to occur. Also, variations in aberrations due to focusing increase, which is not desirable. Also, variations in astigmatic aberrations increase, making the image surface liable to incline to a negative side on a side of shorter working distance.

Also, more preferably the endoscopic objective optical system 1 is configured to satisfy the following conditional expressions:

$$-3 < F\_F/FL < -0.9 \quad (3)$$

$$2.5 < F\_R/FL < 5 \quad (4)$$

where F_F is a focal length of the front group, and F_R is a focal length of the rear group.

Here, conditional expression (3) concerns downsizing of the front group and prescribes the focal length of the front group. When the focal length of the front group is smaller than −3, i.e., the lower limit of conditional expression (3), refractive power of the front group becomes insufficient, and consequently a diameter of a first lens L1 tends to become large. Also, this is disadvantageous for a wider angle of view. When −0.9 i.e., the upper limit of conditional expression (3) is exceeded, this is advantageous for downsizing of lens diameters of each lens, but high order off-axis aberrations become liable to occur. Also, the influence of eccentricity errors on deterioration of optical performance increases, which is not desirable.

Conditional expression (4) concerns ensuring of back focus and prescribes the focal length of the rear group. When the focal length of the rear group is smaller than 2.5, i.e., the lower limit of conditional expression (4), refractive power of the rear group becomes insufficient, which is disadvantageous in ensuring back focus. When 5, i.e., the upper limit of conditional expression (4), is exceeded, this is advantageous in ensuring back focus, but lens size tends to increase, which is not desirable.

A lens having positive or negative refractive power can be used as the focusing lens F, and when the focusing lens F has positive refractive power and the working distance changes from a longer side to a shorter side, preferably focus is set to the side of shorter working distance by moving the focusing lens to the image side.

Also, when the focusing lens F has a negative refractive index and the working distance changes from the longer side to the shorter side, preferably focus is set to the side of shorter working distance by moving the focusing lens F to the object side.

This is because focus can be set to the side of shorter working distance by moving the focusing lens F to the object side along the optical axis.

By satisfying the above conditional expressions, the present invention, reduces variations in aberrations due to manufacturing errors and variations in aberrations due to focusing by prescribing the focal length of the focusing lens while allowing placement of optical members such as a polarizing prism. Specifically, the present invention makes it possible to suppress aberrations due to manufacturing errors, decrease influence on deterioration of optical performance, and, for example, reduce side blur. Also, the present invention makes it possible to suppress variations in aberrations due to focusing, decrease variations in astigmatic aberrations, and prevent an image surface from becoming liable to incline to the negative side on the side of shorter working distance. Note that the focusing lens has a positive or negative weak refractive index, i.e., refractive power.

EXAMPLES

Next, Examples 1 to 8 of the objective optical system according to the first embodiment described above will be described with reference to FIGS. 2 to 32. In lens data described in each example, r is radius of curvature (in mm), d is a surface interval (mm), Nd is a refractive index with respect to line d, and Vd is the Abbe's number with respect to line d.

Example 1

Figure 2:
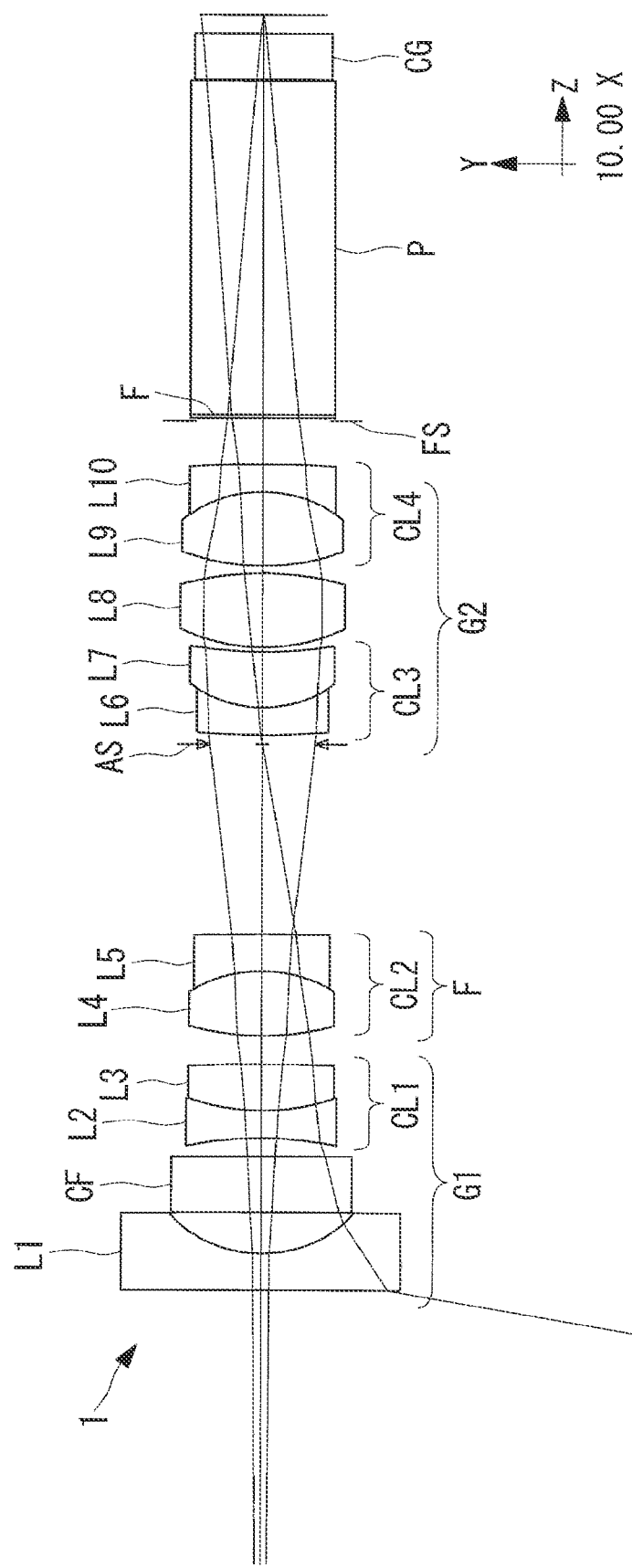
FIG. 2 is a sectional view showing an overall configuration of an objective optical system according to Example 1 of the present invention.
Figure 4:
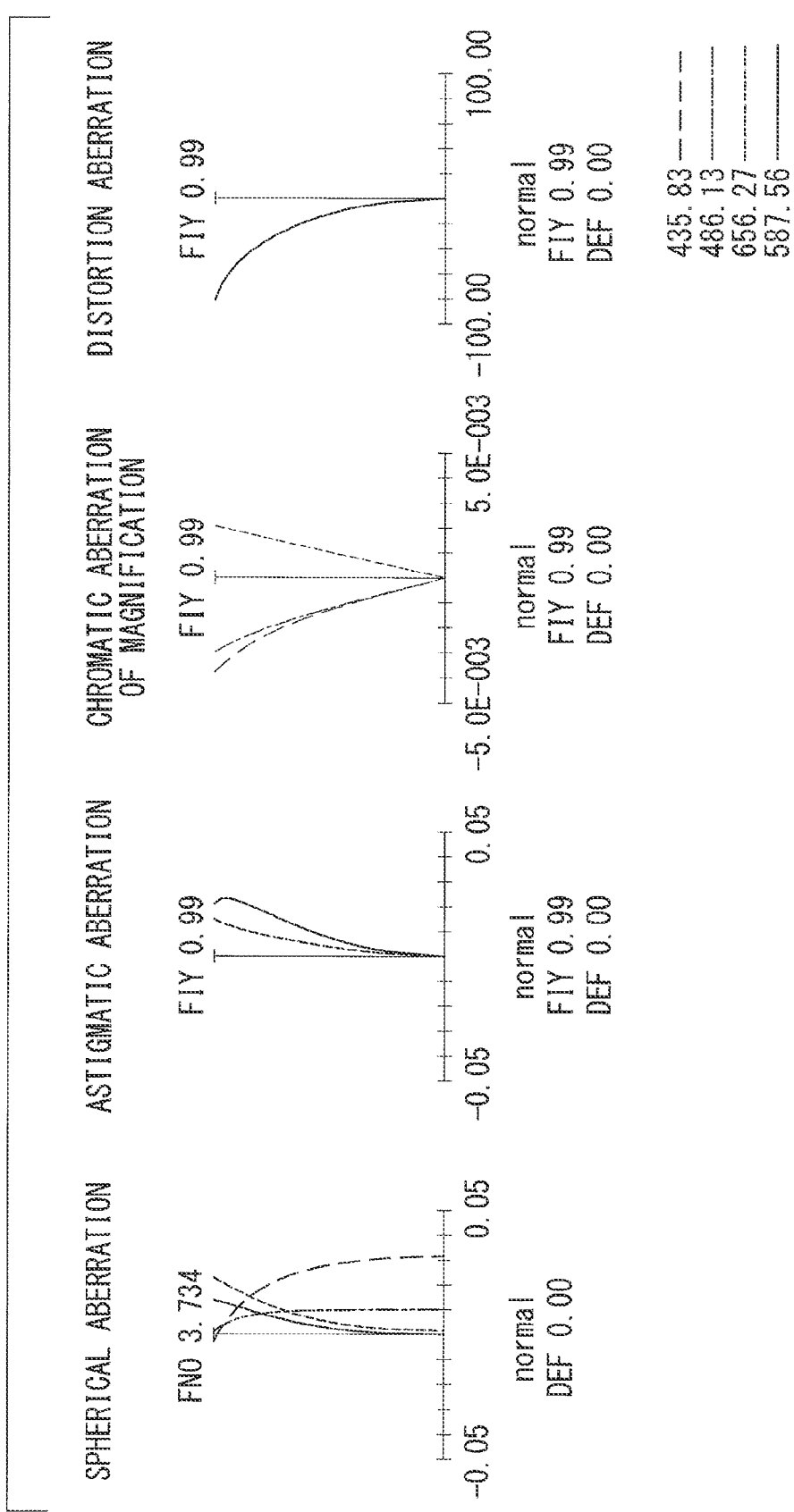
FIG. 4 is an aberration curve in the normal observation mode of the objective optical system of FIG. 3(a).
Figure 5:
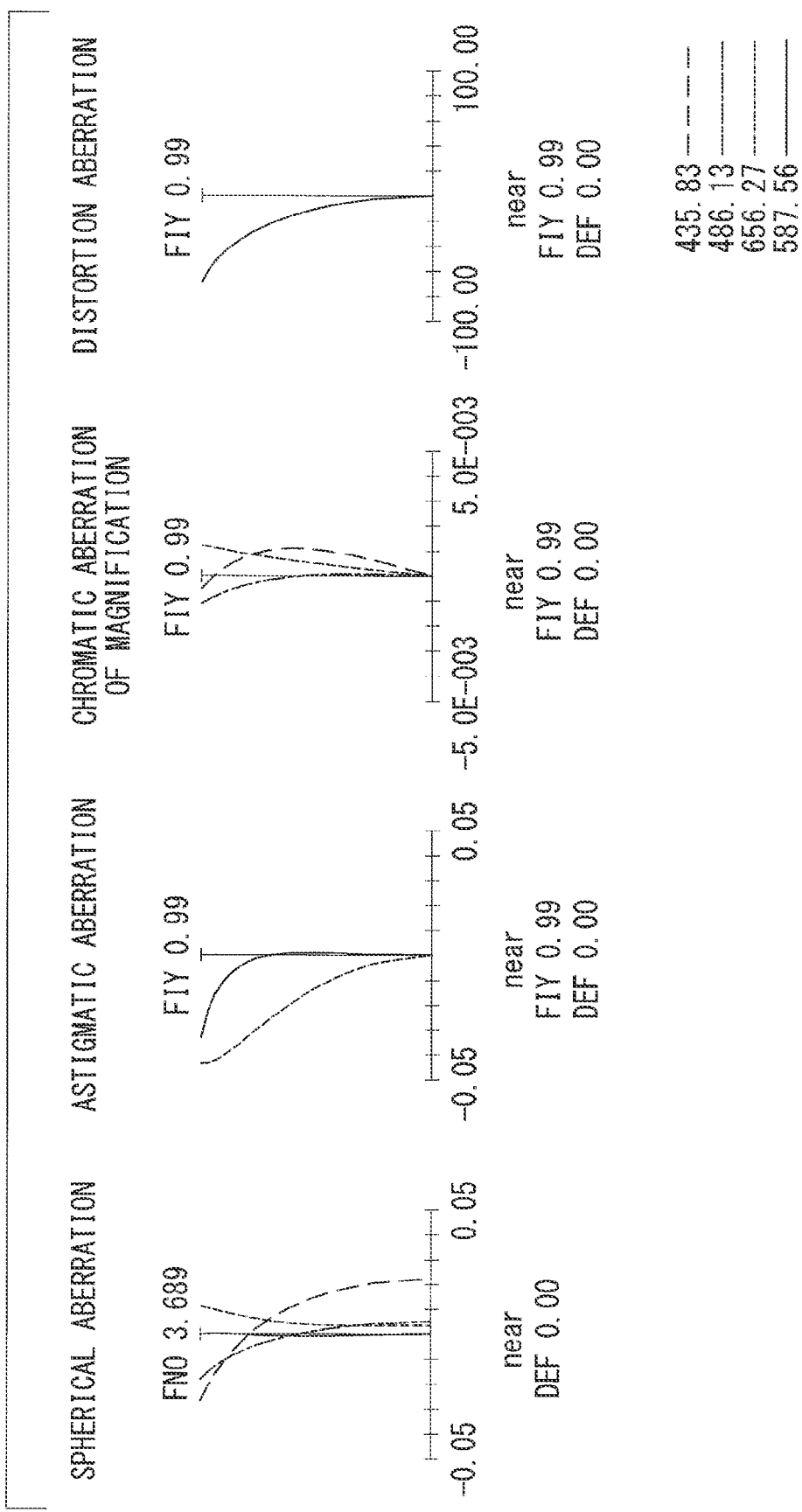
FIG. 5 is an aberration curve in the short distance observation mode of the objective optical system of FIG. 3(b).

A configuration of an endoscopic objective optical system according to Example 1 of the present invention is shown in FIGS. 2 and 3. FIG. 3(a) shows a normal observation mode and FIG. 3(b) shows a short distance observation mode, and rays shown here include on-axis marginal rays and principal rays with a maximum angle of view. Also, an aberration curve in the normal observation mode of the endoscopic objective optical system according to the present example is shown in FIG. 4 and an aberration curve in the short distance observation mode is shown in FIG. 5.

As shown in FIG. 2, in the endoscopic objective optical system 1 according to Example 1, the negative front group G1 includes, in order from the object side, a first lens L1 which is a plano-concave lens with a planar surface on the object side, an infrared cut filter CF, a second lens L2 which is a double-concave lens, and a third lens L3 which is a double-convex lens. Of those lenses, the second lens L2 and third lens L3 are cemented together, forming a cemented lens CL1.

The focusing lens F includes a fourth lens L4 which is a double-convex lens and a fifth lens L5 which is a negative meniscus lens with a concave surface turned to the object side, where the fourth lens L4 and fifth lens L5 are cemented together, forming a cemented lens CL2. The focusing lens F has positive refractive power.

The positive rear group G2 includes, in order from the object side, a sixth lens L6 which is a negative meniscus lens with a concave surface turned to the image side, a seventh lens L7 which is a positive meniscus lens with a concave surface turned to the image side, an eighth lens L8 which is a double-convex lens, a ninth lens L9 which is a double-convex lens, and a tenth lens L10 which is a negative meniscus lens with a concave surface turned to the object side. Of those lenses, the sixth lens L6 and seventh lens L7 are cemented together, forming a cemented lens CL3 and the ninth lens L9 and tenth lens L10 are cemented together, forming a cemented lens CL4.

Also, an aperture stop AS is installed between the focusing lens F and rear group G2.

During short distance observation, the fourth lens L4 and fifth lens L5 which are focusing lenses F move to the image side along the optical axis, setting focus to the side of shorter working distance.

Lens data of the objective optical system according to Example 1 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6321 | 1.88300 | 40.76 |
| 2 | 1.8812 | 0.6957 | 1. | |
| 3(FS) | ∞ | 0.0158 | 1. | |
| 4 | ∞ | 0.9482 | 1.52100 | 65.12 |
| 5 | ∞ | 0.3161 | 1. | |
| 6 | −5.3755 | 0.4741 | 1.88300 | 40.76 |
| 7 | 3.2188 | 0.7902 | 1.58144 | 40.75 |
| 8 | −32.1823 | (d8) | 1. | |
| 9 | 3.9802 | 1.1062 | 1.58267 | 46.42 |
| 10 | −2.0251 | 0.6321 | 1.81600 | 46.62 |
| 11 | −54.4755 | (d11) | 1. | |
| 12(AS) | ∞ | 0.1580 | 1. | |
| 13 | 11.0632 | 0.4741 | 1.88300 | 40.76 |
| 14 | 1.7988 | 0.9482 | 1.80518 | 25.42 |
| 15 | 6.1860 | 0.0790 | 1. | |
| 16 | 2.7854 | 1.2643 | 1.58144 | 40.75 |
| 17 | −4.4702 | 0.1264 | 1. | |
| 18 | 3.3806 | 1.2643 | 1.51823 | 58.90 |
| 19 | −1.8964 | 0.4741 | 1.92286 | 18.90 |
| 20 | −20.5234 | 0.7428 | 1. | |
| 21(FS) | ∞ | 0.0474 | 1. | |
| 22 | ∞ | 0.0522 | 1.53000 | 56.00 |
| 23 | ∞ | 5.7019 | 1.72916 | 54.68 |
| 24 | ∞ | 0.0158 | 1.51000 | 64.00 |
| 25 | ∞ | 0.7902 | 1.61350 | 50.49 |
| 26 | ∞ | 0.3161 | 1. | |
| Image surface | ∞ | 0. | | |

| Lens data | | |
|---|---|---|
| Various data | Normal observation | Short distance observation |
| d0 | 20.40000 | 4.90000 |
| d8 | 0.48991 | 1.03205 |
| d11 | 3.25356 | 2.71142 |

Example 2

Figure 6:
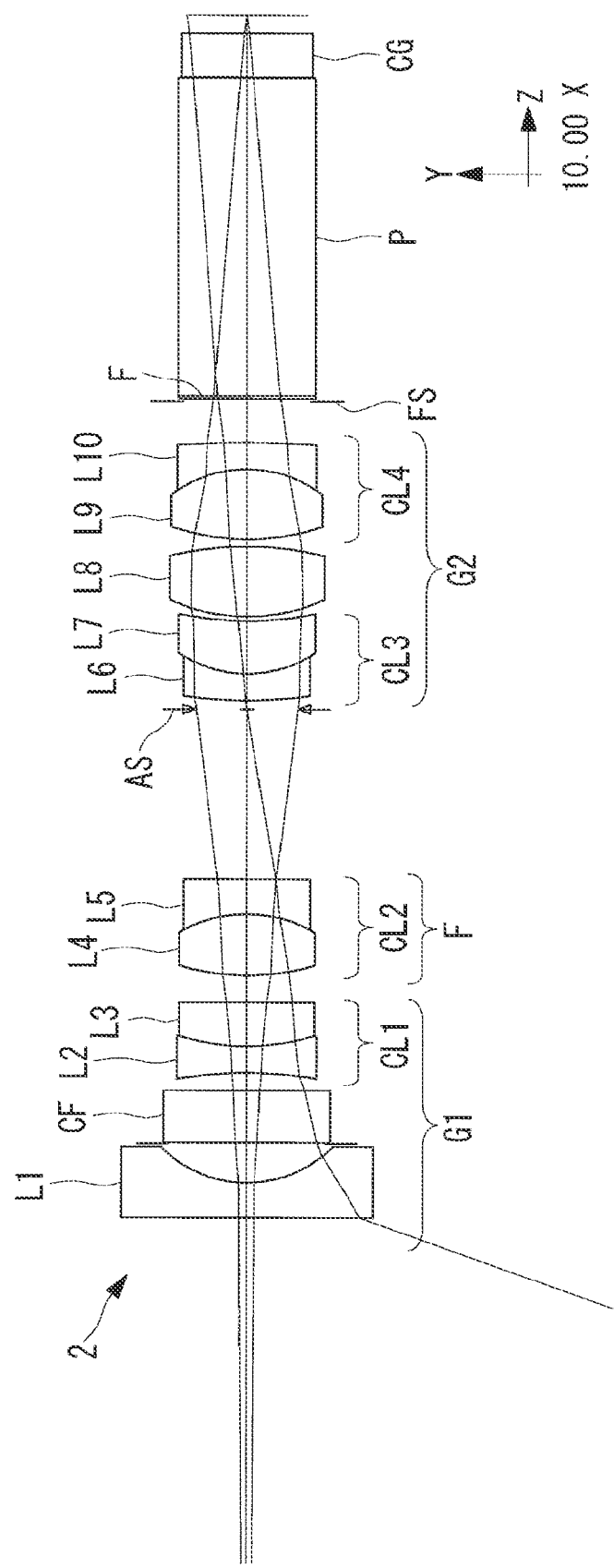
FIG. 6 is a sectional view showing an overall configuration of an objective optical system according to Example 2 of the present invention.
Figure 7:
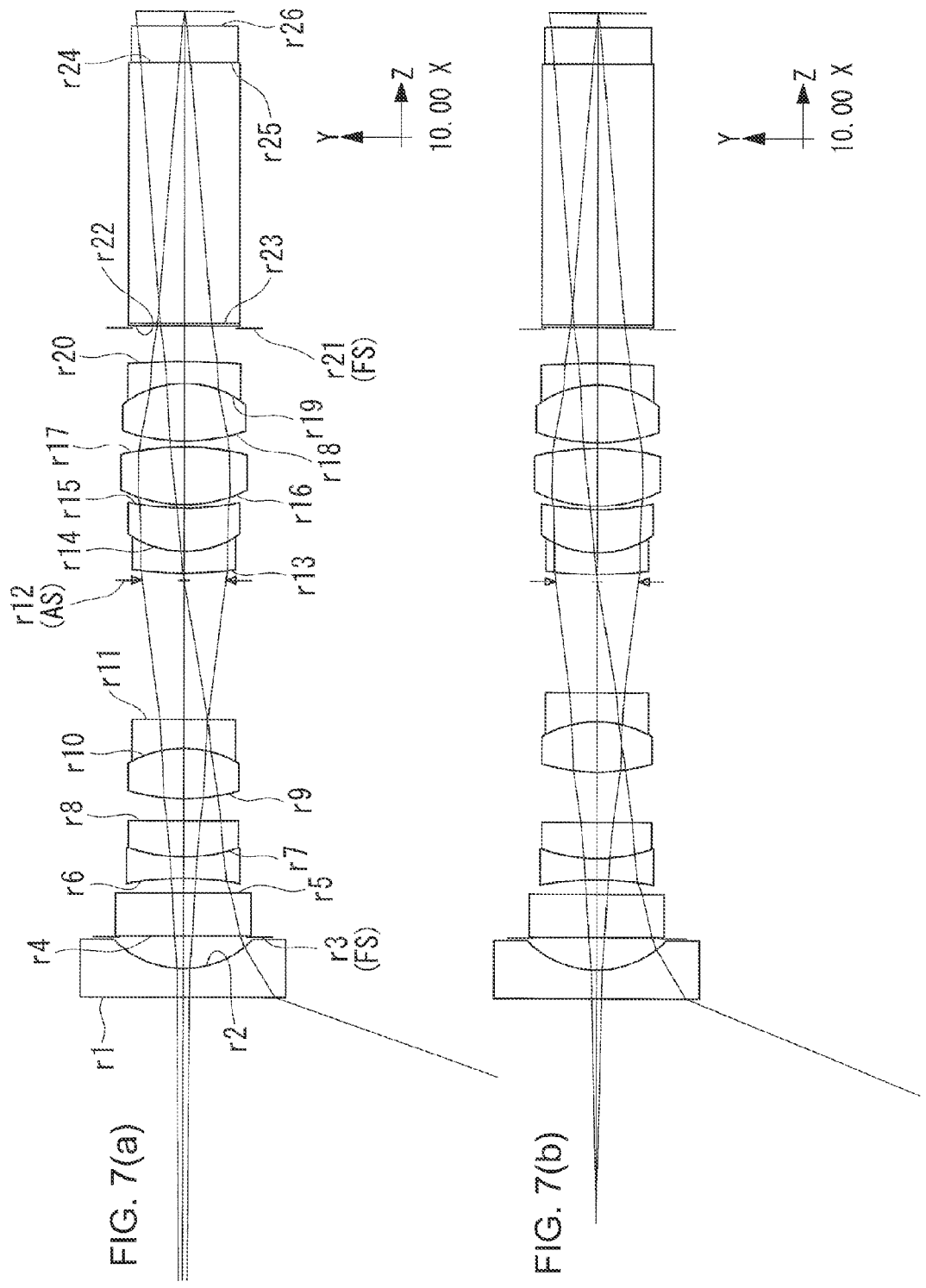
FIGS. 7(a) and 7(b) are sectional views showing the overall configuration of the objective optical system according to Example 2 of the present invention, where
Figure 8:
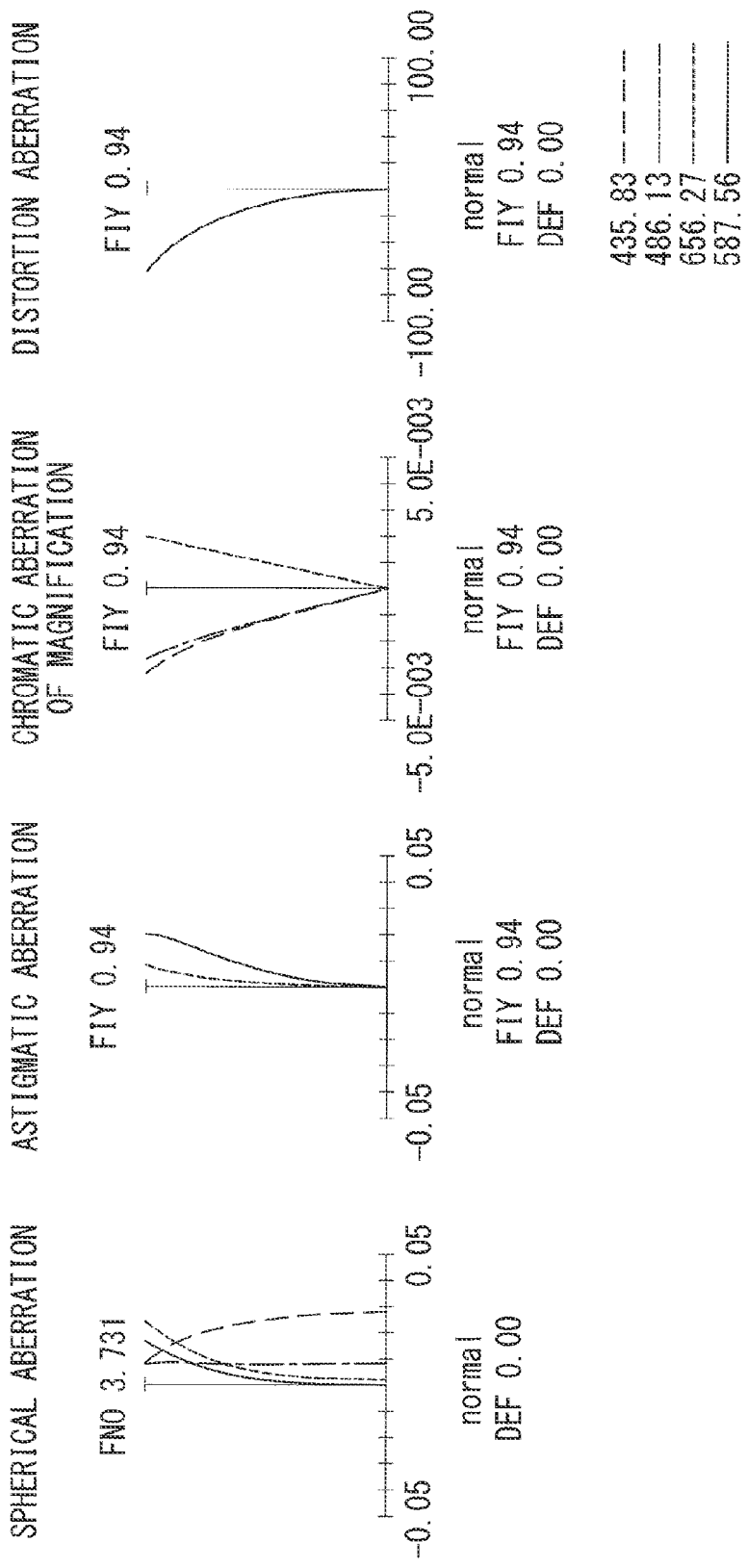
FIG. 8 is an aberration curve in the normal observation mode of the objective optical system of FIG. 7(a).
Figure 9:
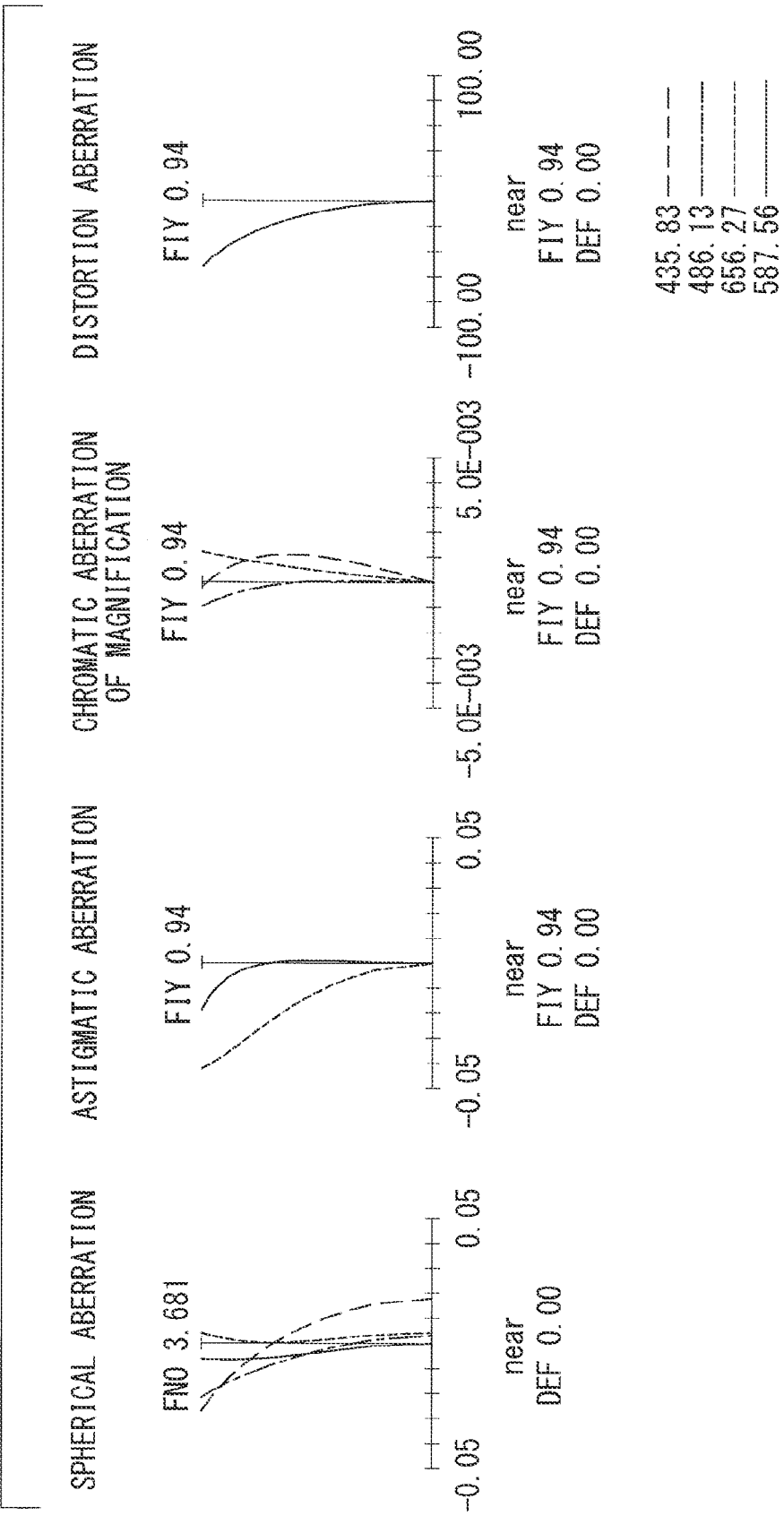
FIG. 9 is an aberration curve in the short distance mode of the objective optical system of FIG. 7(b).

A configuration of an endoscopic objective optical system according to Example 2 of the present invention is shown in FIGS. 6 and 7. FIG. 7(a) shows a normal observation mode and FIG. 7(b) shows a short distance observation mode, and rays shown here include on-axis marginal rays and principal rays with a maximum angle of view. Also, an aberration curve in the normal observation mode of the endoscopic objective optical system according to the present example is shown in FIG. 8 and an aberration curve in the short distance observation mode is shown in FIG. 9.

As shown in FIG. 6, in the endoscopic objective optical system 2 according to Example 2, the negative front group G1 includes, in order from the object side, a first lens L1 which is a plano-concave lens with a planar surface on the object side, an infrared cut filter CF, a second lens L2 which is a double-concave lens, and a third lens L3 which is a double-convex lens. Of those lenses, the second lens L2 and third lens L3 are cemented together, forming a cemented lens CL1.

The focusing lens F includes a fourth lens L4 which is a double-convex lens and a fifth lens L5 which is a double-concave lens, where the fourth lens L4 and fifth lens L5 are cemented together, forming a cemented lens CL2. The focusing lens F has positive refractive power.

The positive rear group G2 includes, in order from the object side, a sixth lens L6 which is a negative meniscus lens with a concave surface turned to the image side, a seventh lens L7 which is a positive meniscus lens with a concave surface turned to the image side, an eighth lens L8 which is a double-convex lens, a ninth lens L9 which is a double-convex lens, and a tenth lens L10 which is a negative meniscus lens with a concave surface turned to the object side. Of those lenses, the sixth lens L6 and seventh lens L7 are cemented together, forming a cemented lens CL3 and the ninth lens L9 and tenth lens L10 are cemented together, forming a cemented lens CL4.

Also, an aperture stop AS is installed between the focusing lens F and rear group G2.

During short distance observation, the fourth lens L4 and fifth lens L5 which are focusing lenses F move to the image side along the optical axis, setting focus to the side of shorter working distance.

Lens data of the objective optical system according to Example 2 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6018 | 1.88300 | 40.76 |
| 2 | 1.7838 | 0.6623 | 1. | |
| 3(FS) | ∞ | 0.0150 | 1. | |
| 4 | ∞ | 0.9027 | 1.52100 | 65.12 |
| 5 | ∞ | 0.3009 | 1. | |

-continued

| Lens data | | | | |
|---|---|---|---|---|
| 6 | −5.8632 | 0.4514 | 1.88300 | 40.76 |
| 7 | 3.0388 | 0.7523 | 1.58144 | 40.75 |
| 8 | −262.6157 | (d8) | 1. | |
| 9 | 3.4555 | 1.0532 | 1.58267 | 46.42 |
| 10 | −1.9593 | 0.6018 | 1.81600 | 46.62 |
| 11 | 188.3682 | (d11) | 1. | |
| 12(AS) | ∞ | 0.1505 | 1. | |
| 13 | 6.6902 | 0.4514 | 1.88300 | 40.76 |
| 14 | 1.7629 | 0.9027 | 1.80518 | 25.42 |
| 15 | 4.8177 | 0.0752 | 1. | |
| 16 | 2.6152 | 1.2037 | 1.58144 | 40.75 |
| 17 | −4.6255 | 0.1204 | 1. | |
| 18 | 3.3881 | 1.2037 | 1.51823 | 58.90 |
| 19 | −1.8055 | 0.4514 | 1.92286 | 18.90 |
| 20 | −14.9878 | 0.7064 | 1. | |
| 21 | ∞ | 0.0451 | 1. | |
| 22 | ∞ | 0.0497 | 1.53000 | 56.00 |
| 23 | ∞ | 5.4285 | 1.72916 | 54.68 |
| 24 | ∞ | 0.0150 | 1.51000 | 64.00 |
| 25 | ∞ | 0.7523 | 1.61062 | 50.49 |
| 26 | ∞ | 0.3009 | 1. | |
| Image surface | ∞ | 0. | | |

| Various data | Normal observation | Short distance observation |
|---|---|---|
| d0 | 19.40000 | 4.70000 |
| d8 | 0.46642 | 1.05683 |
| d11 | 2.91113 | 2.32071 |

Example 3

Figure 10:
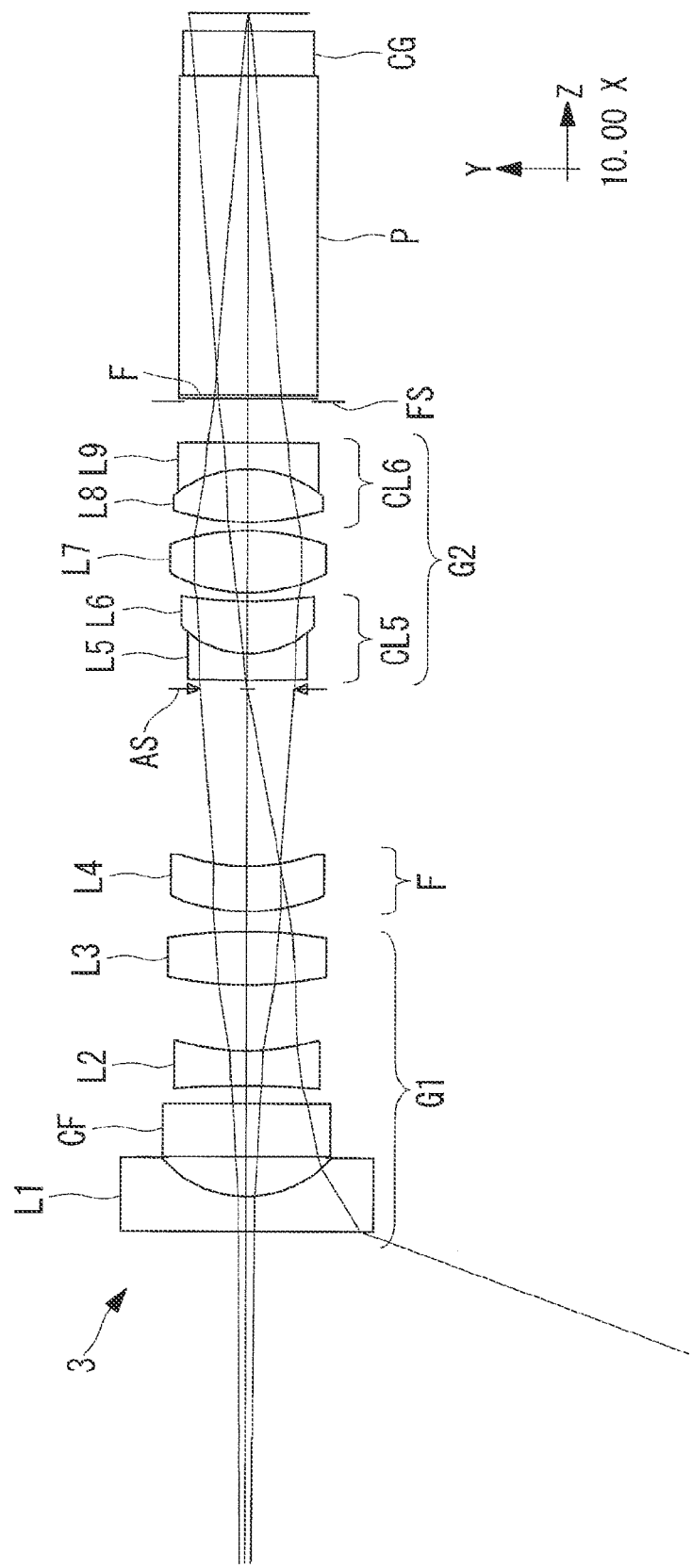
FIG. 10 is a sectional view showing an overall configuration of an objective optical system according to Example 3 of the present invention.
Figure 11:
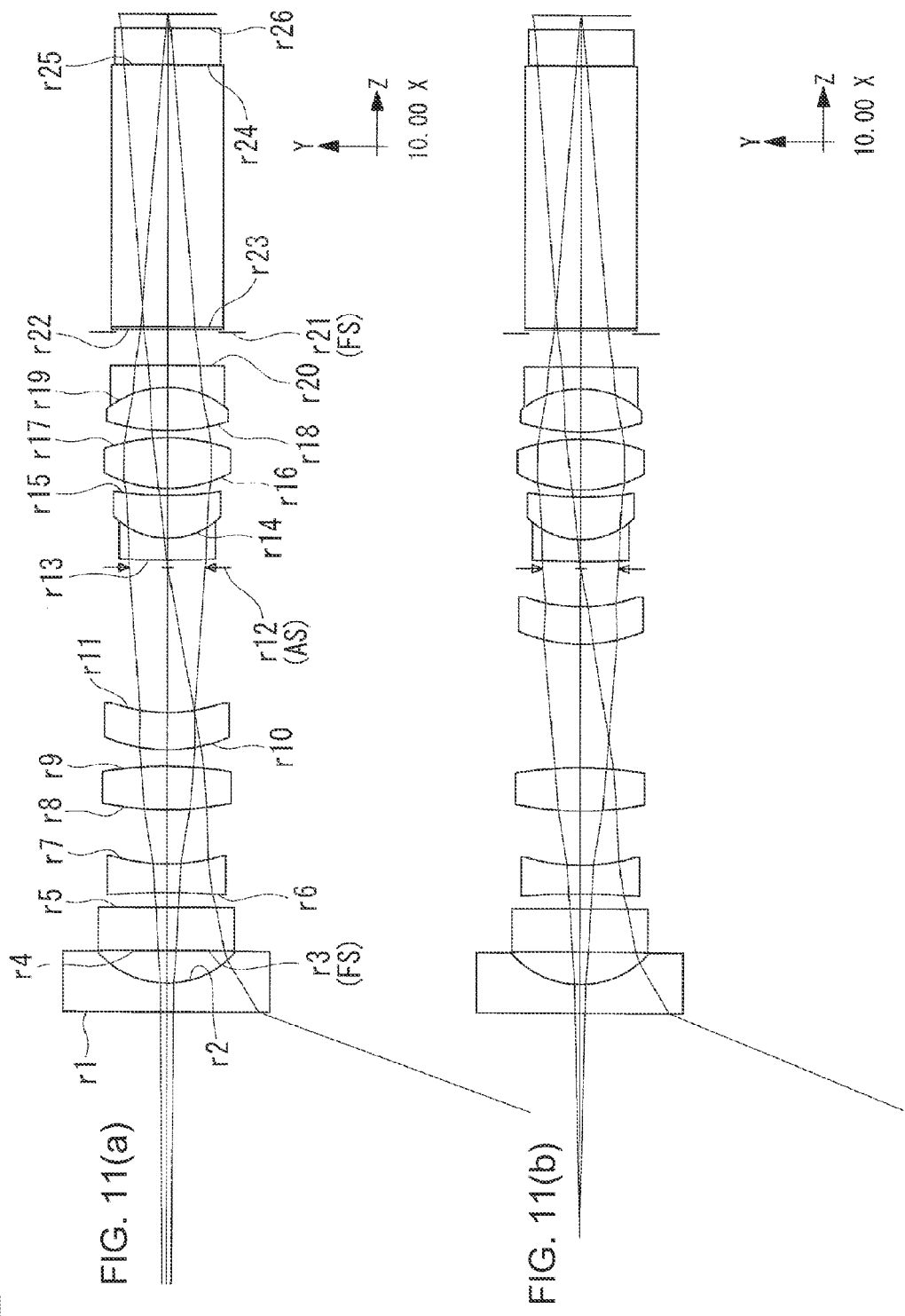
FIGS. 11(a) and 11(b) are sectional views showing the overall configuration of the objective optical system according to Example 3 of the present invention, where
Figure 12:
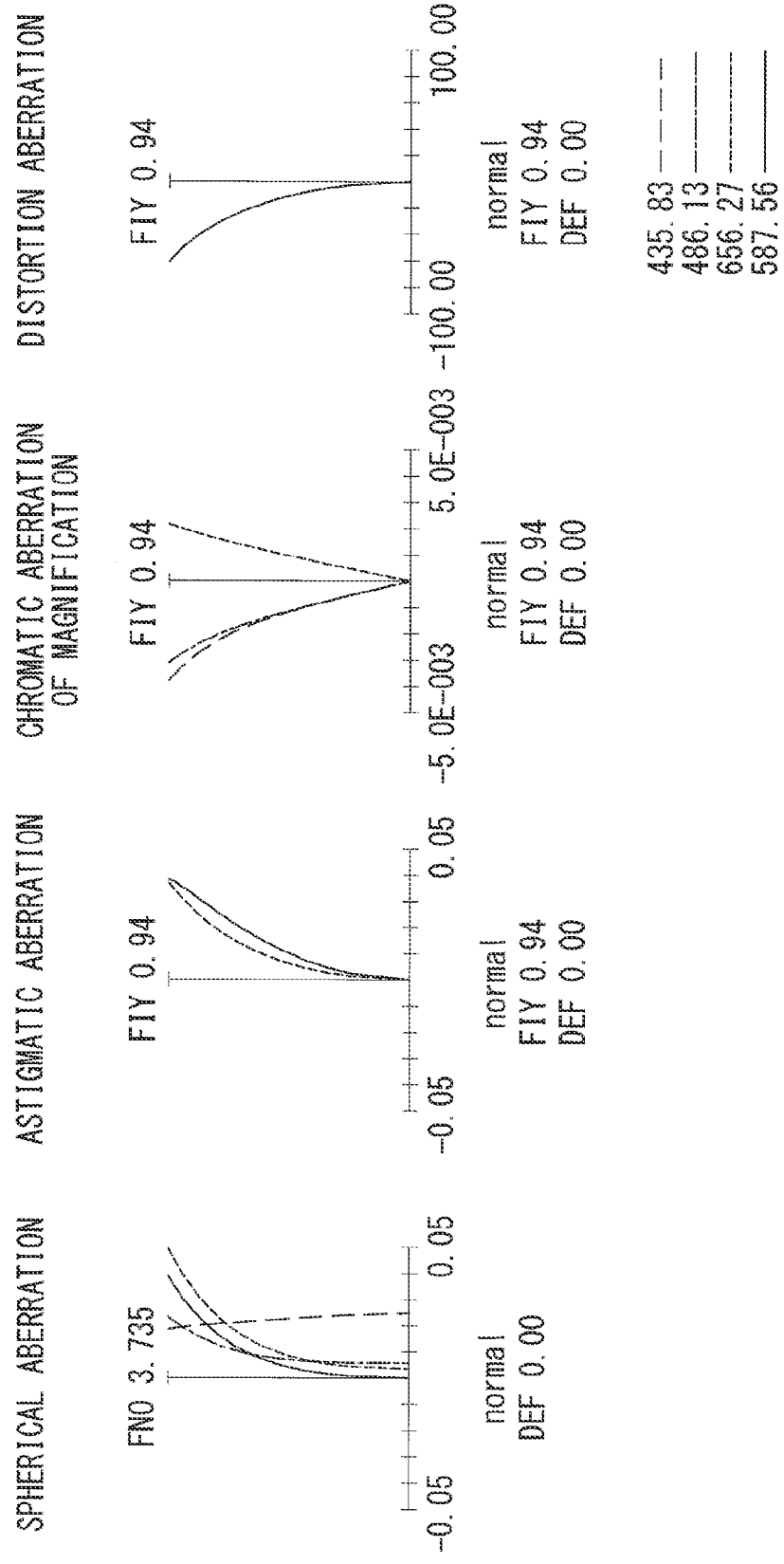
FIG. 12 is an aberration curve in the normal observation mode of the objective optical system of FIG. 11(a).
Figure 13:
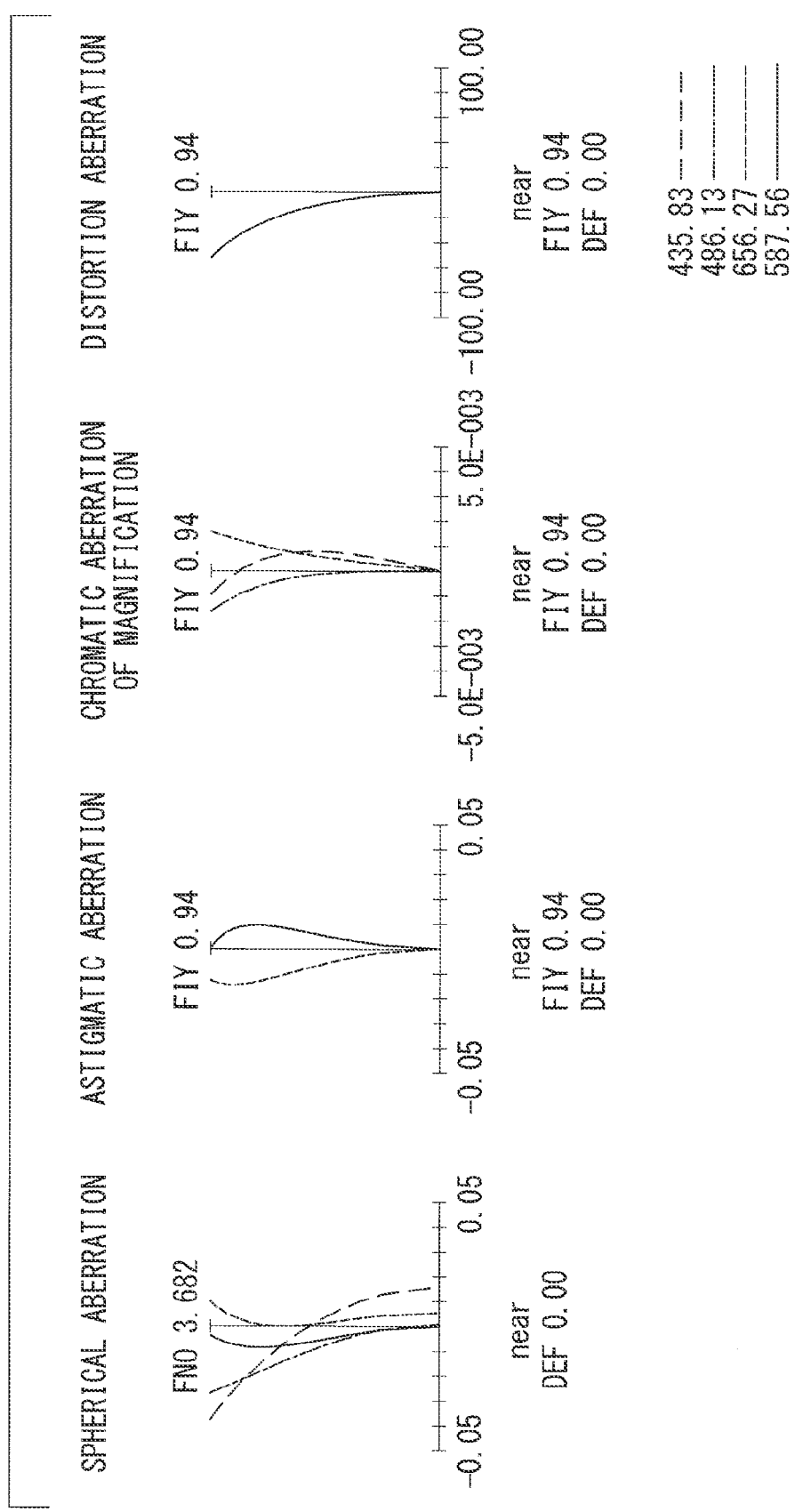
FIG. 13 is an aberration curve in the short distance observation mode of the objective optical system of FIG. 11(b).

A configuration of an endoscopic objective optical system 3 according to Example 3 of the present invention is shown in FIGS. 10 and 11. FIG. 11(a) shows a normal observation mode and FIG. 11(b) shows a short distance observation mode, and rays shown here include on-axis marginal rays and principal rays with a maximum angle of view. Also, an aberration curve in the normal observation mode of the endoscopic objective optical system 3 according to the present example is shown in FIG. 12 and an aberration curve in the short distance observation mode is shown in FIG. 13.

As shown in FIG. 10, in the endoscopic objective optical system 3 according to Example 3, the negative front group G1 includes, in order from the object side, a first lens L1 which is a plano-concave lens with a planar surface on the object side, an infrared cut filter CF, a second lens L2 which is a double-concave lens, and a third lens L3 which is a double-convex lens.

The focusing lens F is a fourth lens L4, which is a positive meniscus lens with a convex surface turned to the object side, and has positive refractive power.

Also, a positive rear group includes a fifth lens L5 which is a negative meniscus lens with a concave surface turned to the image side, a sixth lens L6 which is a positive meniscus lens with a concave surface turned to the image side, a seventh lens L7 which is a double-convex lens, an eighth lens L8 which is a double-convex lens, and a ninth lens L9 which is a negative meniscus lens with a concave surface turned to the object side. Of those lenses, the fifth lens L5 and sixth lens L6 are cemented together, forming a cemented lens CL5 and the eighth lens L8 and ninth lens L9 are cemented together, forming a cemented lens CL6.

Also, an aperture stop AS is installed between the focusing lens F and rear group G2.

During short distance observation, the fourth lens L4 which is a focusing lens F moves to the image side along the optical axis, setting focus to the side of shorter working distance.

Lens data of the endoscopic objective optical system 3 according to Example 3 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6034 | 1.88300 | 40.76 |
| 2 | 1.6946 | 0.6640 | 1. | |
| 3(FS) | ∞ | 0.0151 | 1. | |
| 4 | ∞ | 0.9051 | 1.52100 | 65.12 |
| 5 | ∞ | 0.3017 | 1. | |
| 6 | −16.6193 | 0.6034 | 1.88300 | 40.76 |
| 7 | 3.5630 | 1.1341 | 1. | |
| 8 | 5.9529 | 0.9049 | 1.53172 | 48.84 |
| 9 | −7.5210 | (d9) | 1. | |
| 10 | 2.8889 | 0.7780 | 1.49700 | 81.54 |
| 11 | 2.9891 | (d11) | 1. | |
| 12(AS) | ∞ | 0.1508 | 1. | |
| 13 | 21.2097 | 0.4532 | 1.88300 | 40.76 |
| 14 | 1.3996 | 0.8955 | 1.80518 | 25.42 |
| 15 | 6.6235 | 0.1438 | 1. | |
| 16 | 2.4518 | 1.0559 | 1.53172 | 48.84 |
| 17 | −3.4187 | 0.1508 | 1. | |
| 18 | 3.6407 | 0.9051 | 1.58144 | 40.75 |
| 19 | −1.7430 | 0.4572 | 1.92286 | 18.90 |
| 20 | −91.7614 | 0.6946 | 1. | |
| 21(FS) | ∞ | 0.0588 | 1. | |
| 22 | ∞ | 0.0498 | 1.53000 | 56.00 |
| 23 | ∞ | 5.4425 | 1.72916 | 54.68 |
| 24 | ∞ | 0.0151 | 1.51000 | 64.00 |
| 25 | ∞ | 0.7542 | 1.61062 | 50.49 |
| 26 | ∞ | 0.3017 | 1. | |
| Image surface | ∞ | 0. | | |

| Various data | Normal observation | Short distance observation |
|---|---|---|
| d0 | 19.40000 | 4.70000 |
| d9 | 0.34913 | 2.58407 |
| d11 | 3.02798 | 0.79304 |

Example 4

Figure 14:
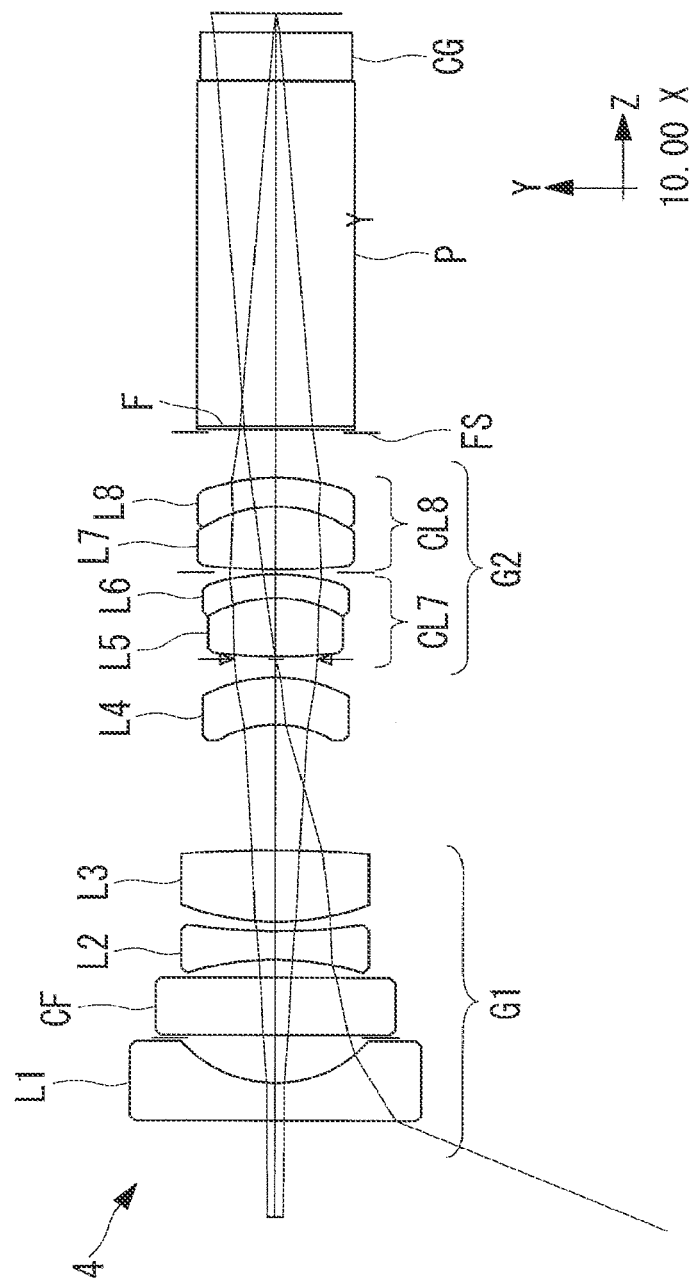
FIG. 14 is a sectional view showing an overall configuration of an objective optical system according to Example 4 of the present invention.
Figure 15:
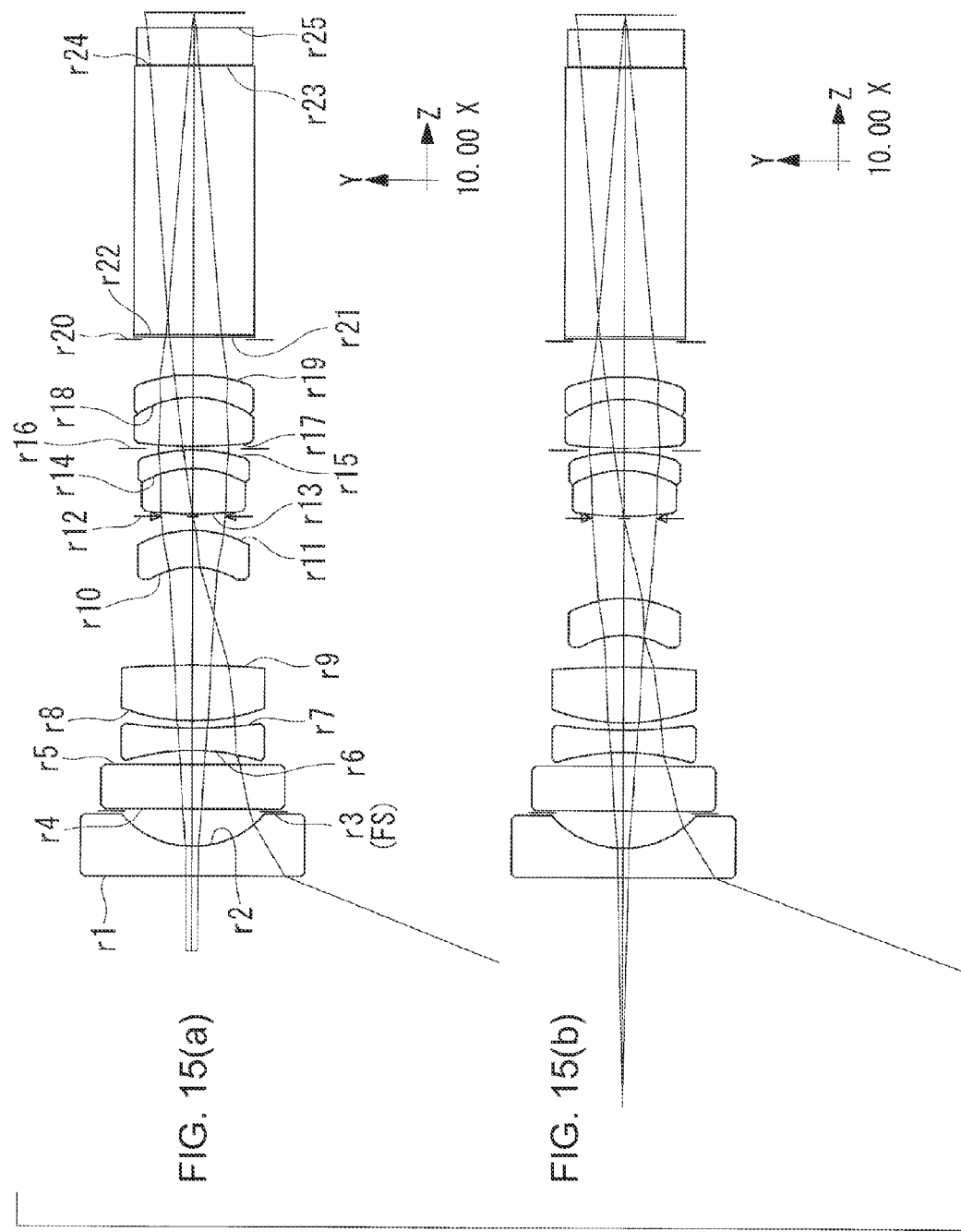
FIGS. 15(a) and 15(b) are sectional views showing the overall configuration of the objective optical system according to Example 4 of the present invention, where
Figure 16:
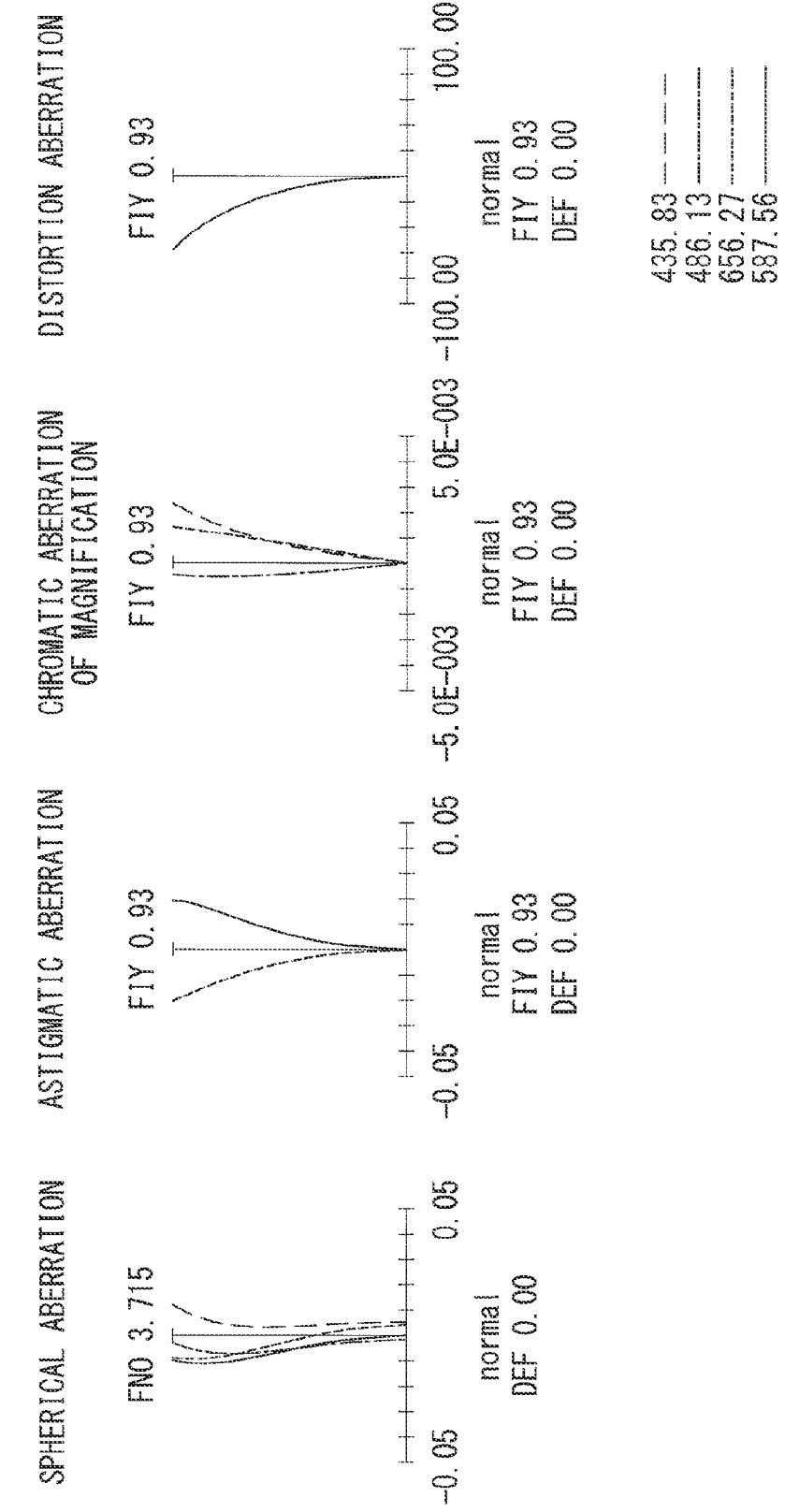
FIG. 16 is an aberration curve in the normal observation mode of the objective optical system of FIG. 15(a).
Figure 17:
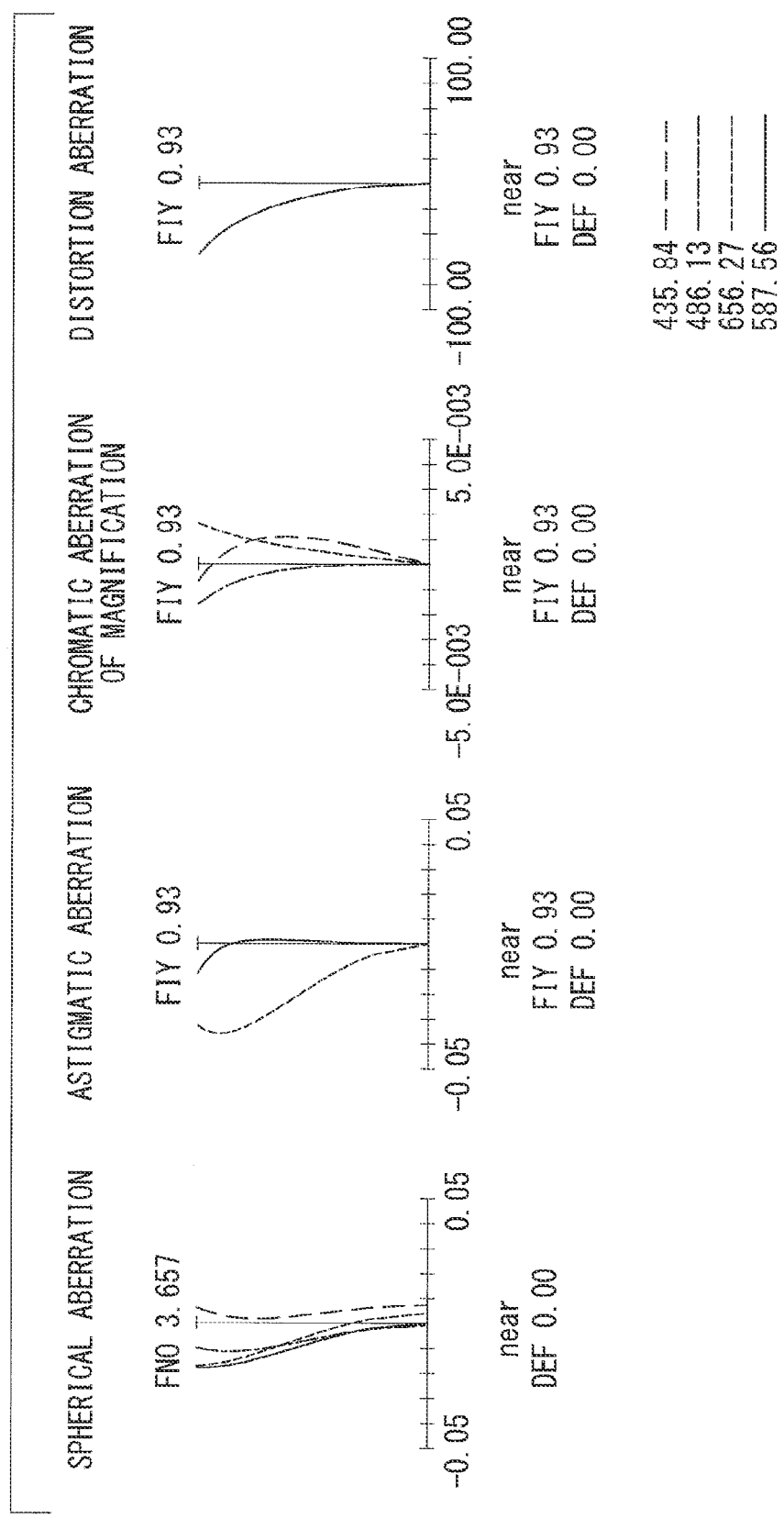
FIG. 17 is an aberration curve in the short distance observation mode of the objective optical system of FIG. 15(b).

A configuration of an endoscopic objective optical system 4 according to Example 4 of the present invention is shown in FIGS. 14 and 15. FIG. 15(a) shows a normal observation mode and FIG. 15(b) shows a short distance observation mode, and rays shown here include on-axis marginal rays and principal rays with a maximum angle of view. Also, an aberration curve in the normal observation mode of the endoscopic objective optical system 4 according to the present example is shown in FIG. 16 and an aberration curve in the short distance observation mode is shown in FIG. 17.

As shown in FIG. 14, in the endoscopic objective optical system 4 according to Example 4, the negative front group G1 includes, in order from the object side, a first lens L1 which is a plano-concave lens with a planar surface on the object side, an infrared cut filter CF, a second lens L2 which is a double-concave lens, and a third lens L3 which is a double-convex lens.

The focusing lens F is a fourth lens L4, which is a negative meniscus lens with a concave surface turned to the object side, and has negative refractive power.

The positive rear group G2 includes, in order from the object side, a fifth lens L5 which is a double-convex lens, a sixth lens L6 which is a negative meniscus lens with a concave surface turned to the object side, a seventh lens L7 which is a double-convex lens, and an eighth lens L8 which is a negative meniscus lens with a concave surface turned to the object side. Of those lenses, the fifth lens L5 and sixth lens L6 are cemented together, forming a cemented lens CL7 and the seventh lens L7 and eighth lens L8 are cemented together, forming a cemented lens CL8.

Also, an aperture stop AS is installed between the focusing lens F and rear group G2.

During short distance observation, the fourth lens L4 which is a focusing lens F moves to the object side along the optical axis, setting focus to the side of shorter working distance.

Lens data of the endoscopic objective optical system 4 according to Example 4 of the present invention is shown below.

| Lens data | | | | |
|---|---|---|---|---|
| Surface number | r | d | Nd | Vd |
| Object surface | ∞ | (d0) | 1. | |
| 1 | ∞ | 0.5967 | 1.88300 | 40.76 |
| 2 | 1.7036 | 0.7062 | 1. | |
| 3(FS) | ∞ | 0.0448 | 1. | |
| 4 | ∞ | 0.8951 | 1.51800 | 75.00 |
| 5 | ∞ | 0.2796 | 1. | |
| 6 | −4.0284 | 0.4485 | 1.88300 | 40.76 |
| 7 | 8.3388 | 0.1466 | 1. | |
| 8 | 3.5894 | 1.1194 | 1.92286 | 18.90 |
| 9 | −15.8261 | (d9) | 1. | |
| 10 | −1.5081 | 0.7401 | 1.77529 | 51.13 |
| 11 | −2.0343 | (d11) | 1. | |
| 12(AS) | ∞ | 0.0448 | 1. | |
| 13 | 7.3029 | 0.9108 | 1.50217 | 57.99 |
| 14 | −1.8150 | 0.3729 | 1.95857 | 32.95 |
| 15 | −2.9271 | 0.0298 | 1. | |
| 16(FS) | ∞ | 0.0448 | 1. | |
| 17 | 9.1509 | 0.9811 | 1.52890 | 45.11 |
| 18 | −1.8128 | 0.4475 | 1.92286 | 18.90 |
| 19 | −2.8699 | 0.7099 | 1. | |
| 20(FS) | ∞ | 0.0448 | 1. | |
| 21 | ∞ | 0.0492 | 1.53000 | 56.00 |
| 22 | ∞ | 5.3823 | 1.72916 | 54.68 |
| 23 | ∞ | 0.0149 | 1.51000 | 64.00 |
| 24 | ∞ | 0.7459 | 1.61062 | 50.49 |
| 25 | ∞ | 0.2984 | 1. | |
| Image surface | ∞ | 0. | | |

| Various data | Normal observation | Short distance observation |
|---|---|---|
| d0 | 19.20000 | 4.60000 |
| d9 | 1.96471 | 0.63955 |
| d11 | 0.28250 | 1.60767 |

Example 5

Figure 18:
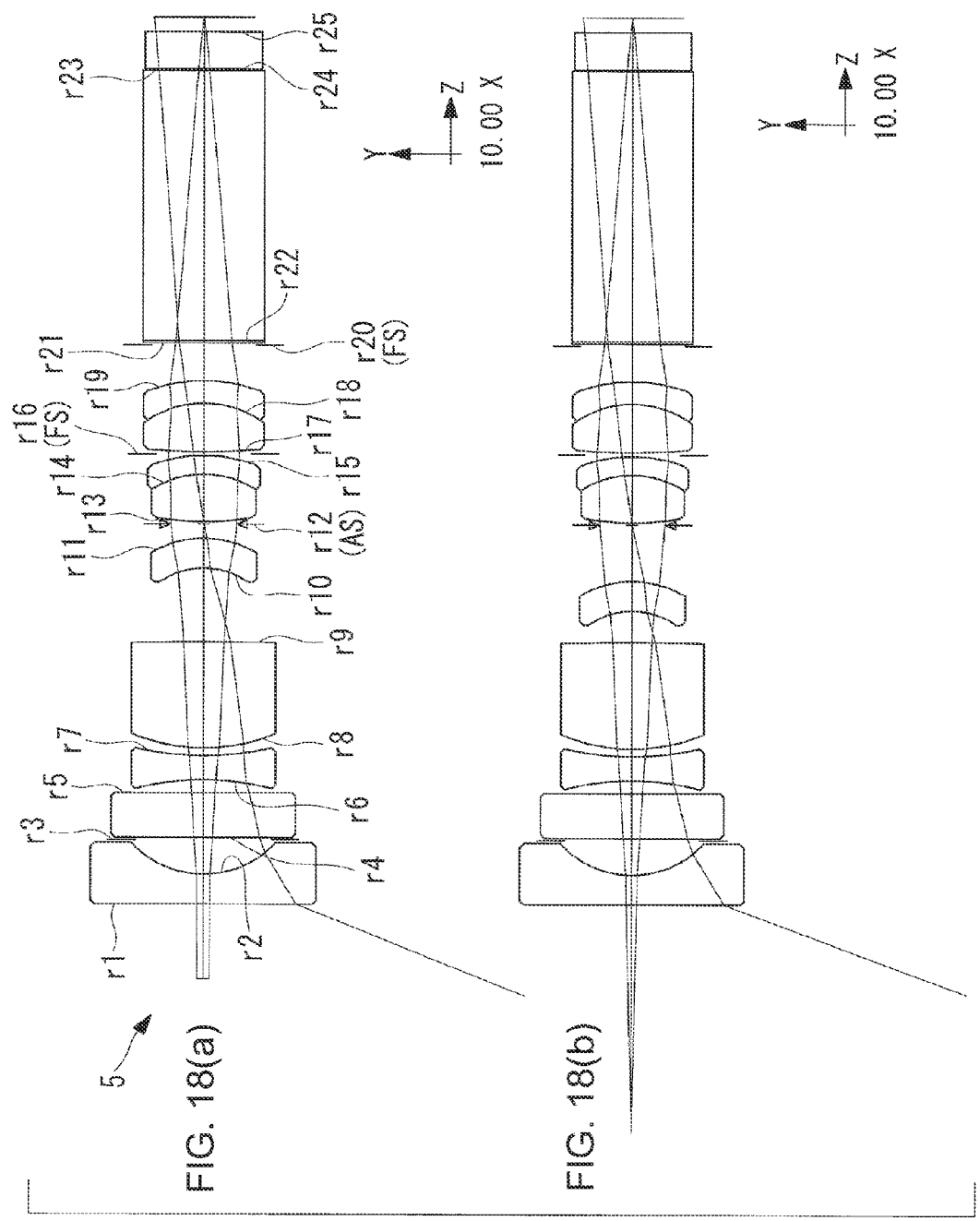
FIGS. 18(a) and 18(b) are sectional views showing the overall configuration of the objective optical system according to Example 5 of the present invention, where
Figure 19:
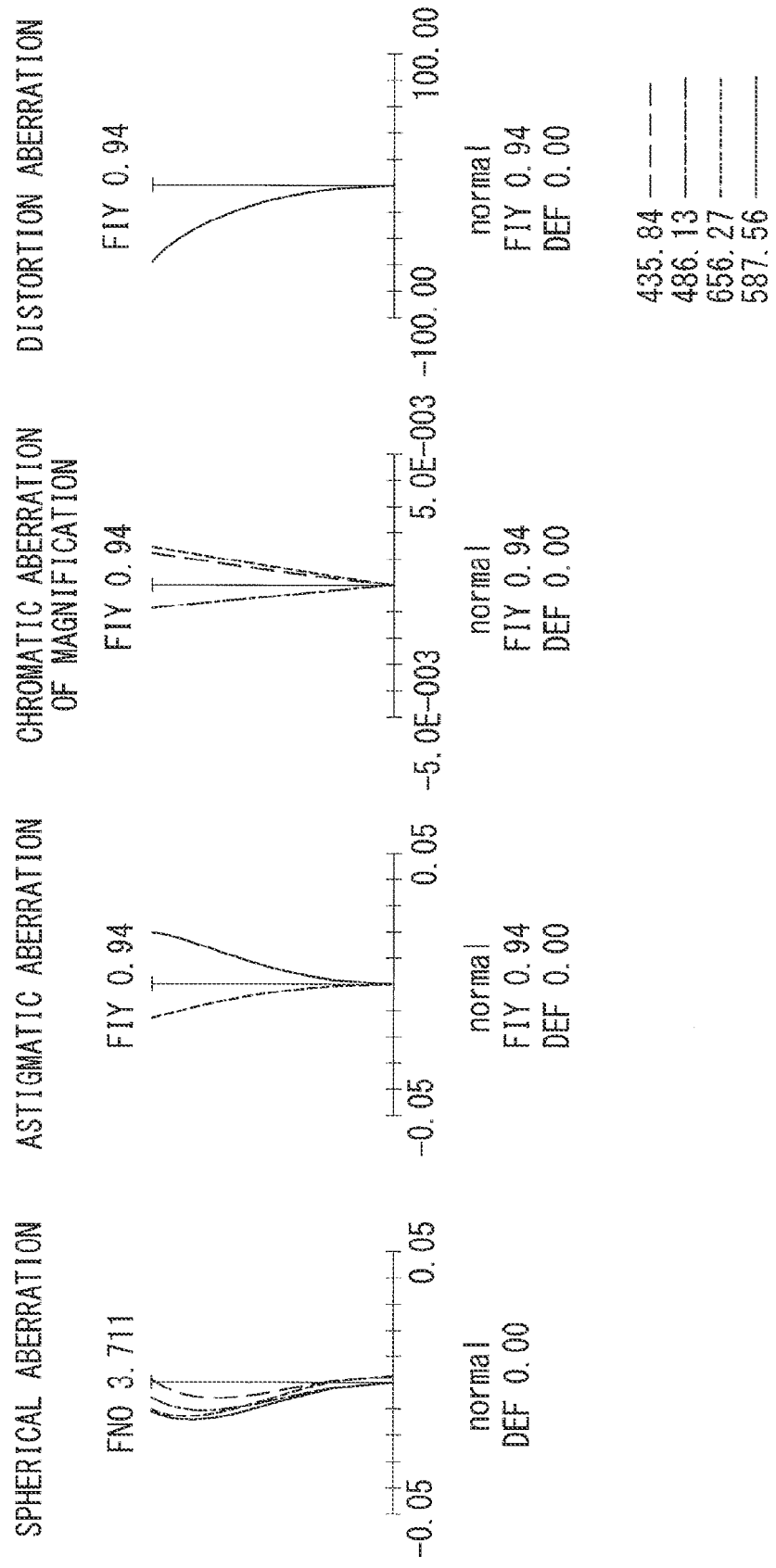
FIG. 19 is an aberration curve in the normal observation mode of the objective optical system of FIG. 18(a).
Figure 20:
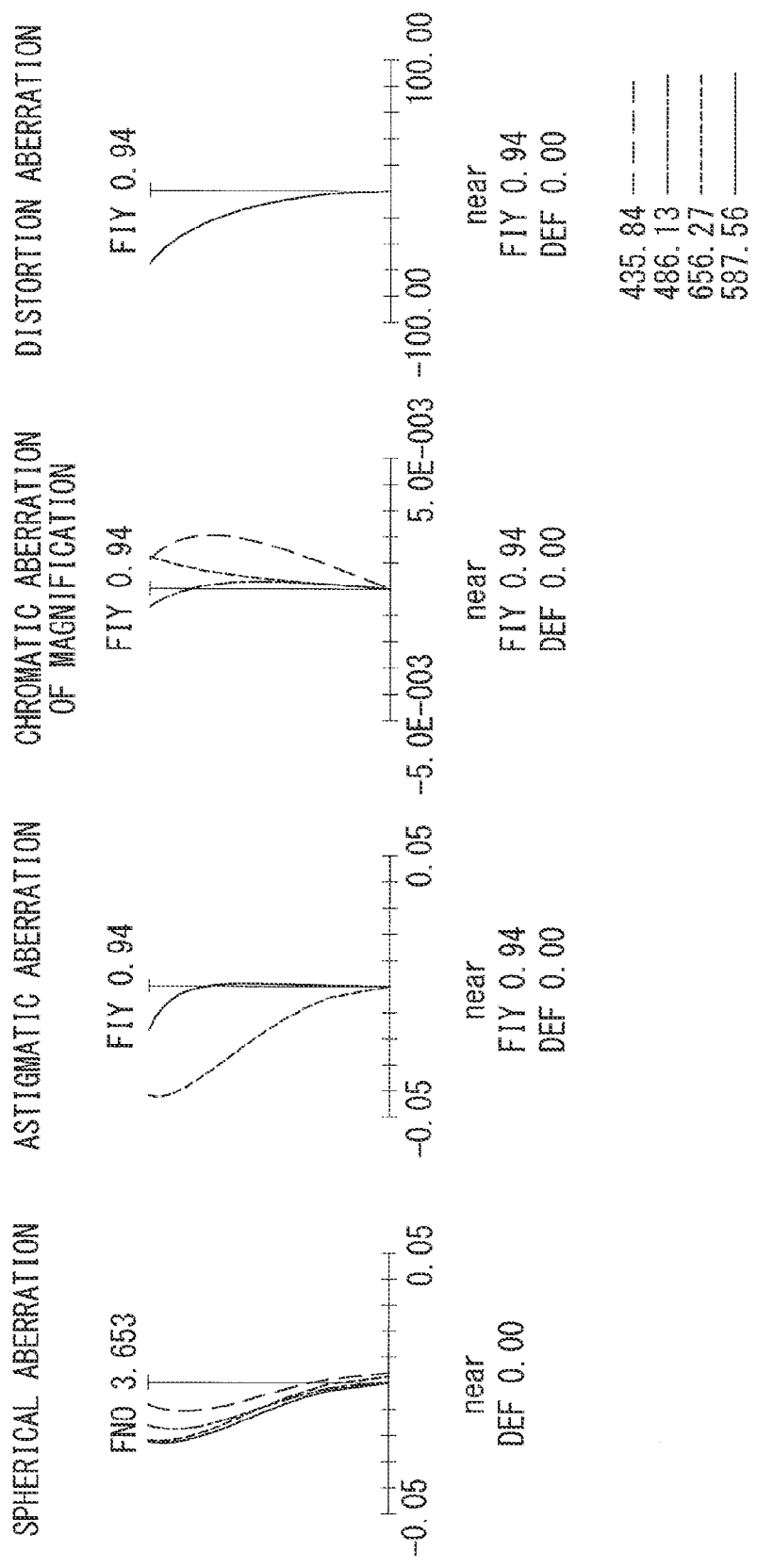
FIG. 20 is an aberration curve in the short distance observation mode of the objective optical system of FIG. 18(b).

A configuration of an endoscopic objective optical system 5 according to Example 5 of the present invention is shown in FIG. 18. Shapes of the lenses making up the endoscopic objective optical system 5 according to Example 5 are the same as Example 4, and thus description thereof will be omitted. FIG. 18(a) shows a normal observation mode and FIG. 18(b) shows a short distance observation mode, and rays shown here include on-axis marginal rays and principal rays with a maximum angle of view. Also, an aberration curve in the normal observation mode of the endoscopic objective optical system according to the present example is shown in FIG. 19 and an aberration curve in the short distance observation mode is shown in FIG. 20.

Lens data of the objective optical system according to Example 5 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6019 | 1.88300 | 40.76 |
| 2 | 1.7554 | 0.6970 | 1. | |
| 3(FS) | ∞ | 0.0451 | 1. | |
| 4 | ∞ | 0.9029 | 1.51800 | 75.00 |
| 5 | ∞ | 0.2599 | 1. | |
| 6 | −4.5983 | 0.4843 | 1.88300 | 40.76 |
| 7 | 5.2759 | 0.1540 | 1. | |
| 8 | 3.2577 | 2.1439 | 1.92286 | 18.90 |
| 9 | −45.0144 | (d9) | 1. | |
| 10 | −1.3809 | 0.6003 | 1.65160 | 58.55 |
| 11 | −1.8282 | (d11) | 1. | |
| 12(AS) | ∞ | 0.0451 | 1. | |
| 13 | 4.9232 | 0.9551 | 1.48749 | 70.23 |
| 14 | −1.7032 | 0.3762 | 1.88300 | 40.76 |
| 15 | −2.5955 | 0.0301 | 1. | |
| 16(FS) | ∞ | 0.0451 | 1. | |
| 17 | 11.1469 | 0.9767 | 1.48749 | 70.23 |
| 18 | −1.7938 | 0.4514 | 2.00330 | 28.27 |
| 19 | −2.8063 | 0.7162 | 1. | |
| 20(FS | )∞ | 0.0451 | 1. | |
| 21 | ∞ | 0.0497 | 1.53000 | 56.00 |
| 22 | ∞ | 5.4293 | 1.72916 | 54.68 |
| 23 | ∞ | 0.0150 | 1.51000 | 64.00 |
| 24 | ∞ | 0.7524 | 1.61062 | 50.491 |
| 25 | ∞ | 0.3010 | 1. | |
| Image surface | ∞ | 0. | | |

| Various data | Normal observation | Short distance observation |
|---|---|---|
| d0 | 19.40000 | 4.60000 |
| d9 | 1.48113 | 0.63434 |
| d11 | 0.28799 | 1.13479 |

Example 6

Figure 21:
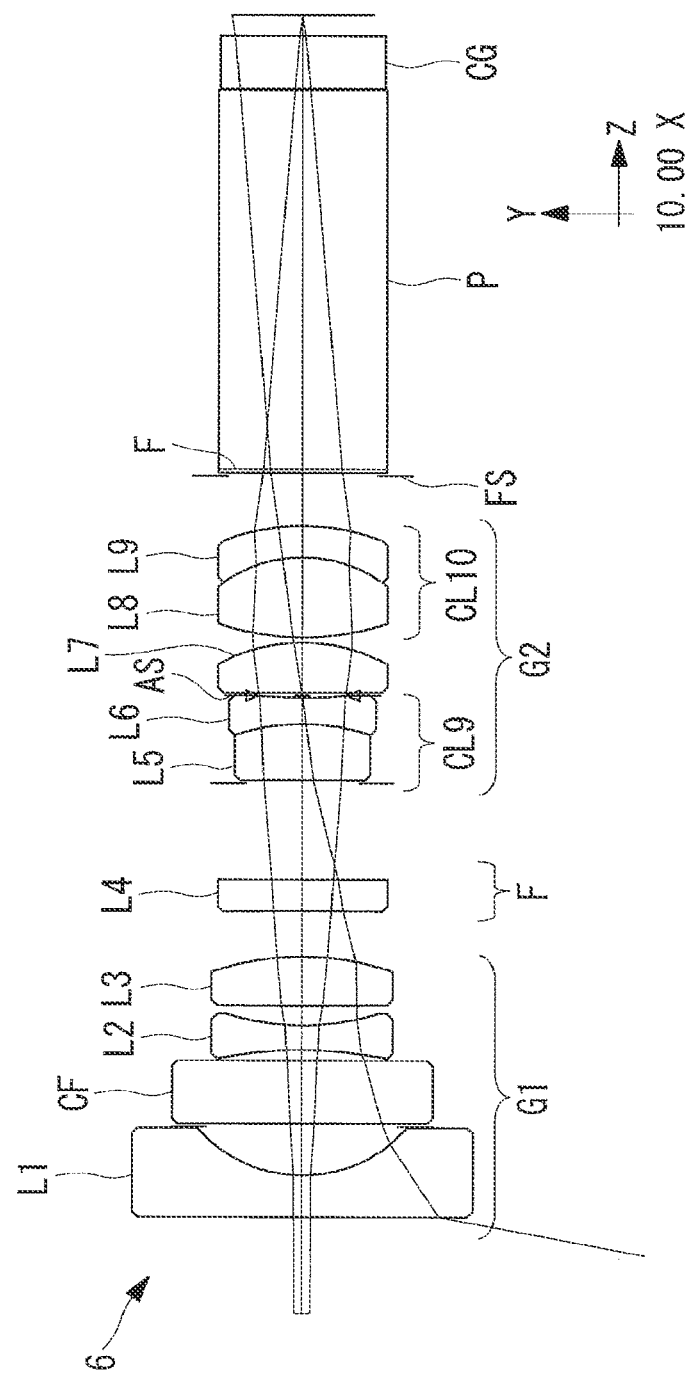
FIG. 21 is a sectional view showing an overall configuration of an objective optical system according to Example 6 of the present invention.
Figure 22:
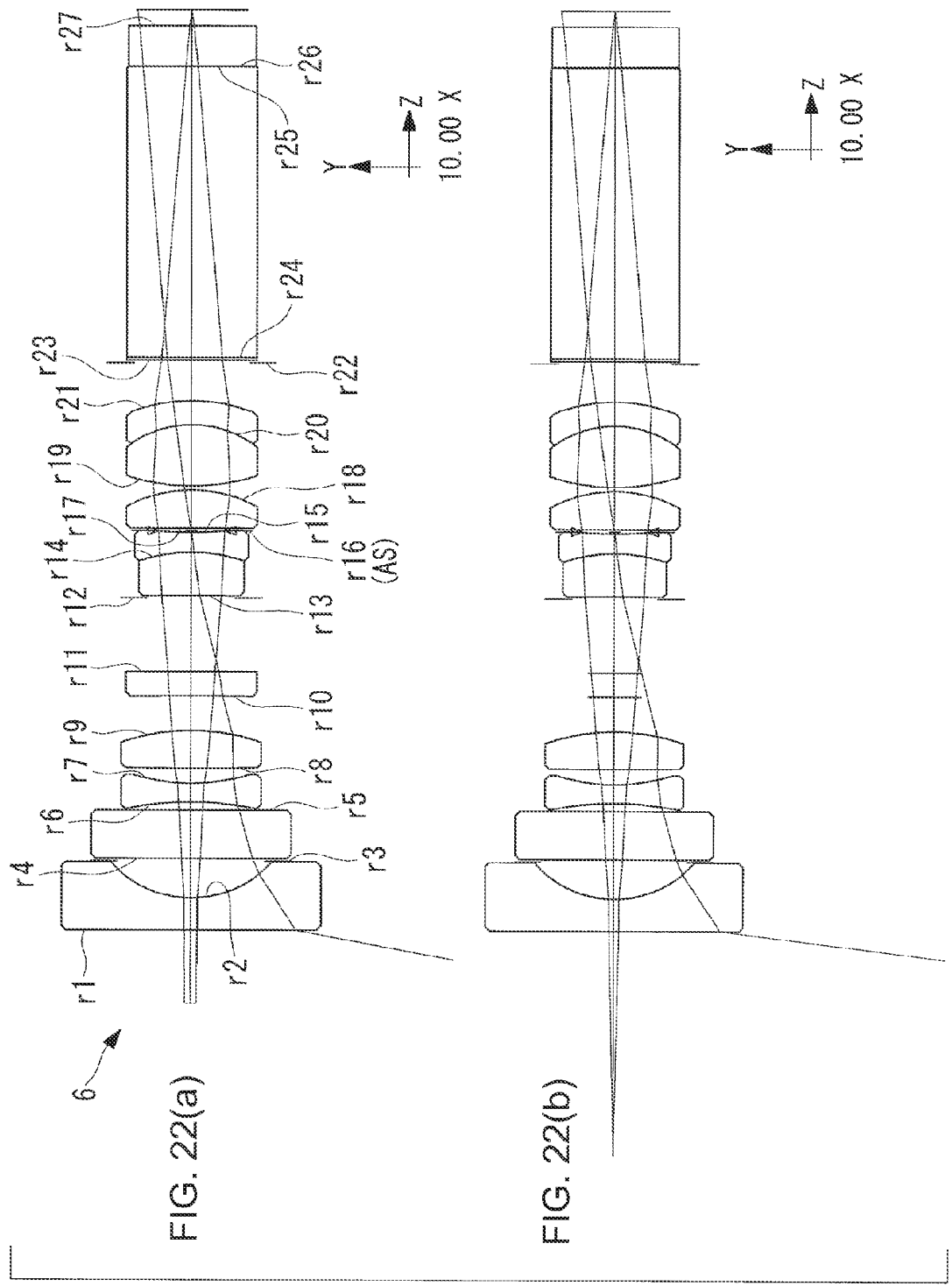
FIGS. 22(a) and 22(b) are sectional views showing the overall configuration of the objective optical system according to Example 6 of the present invention, where
Figure 23:
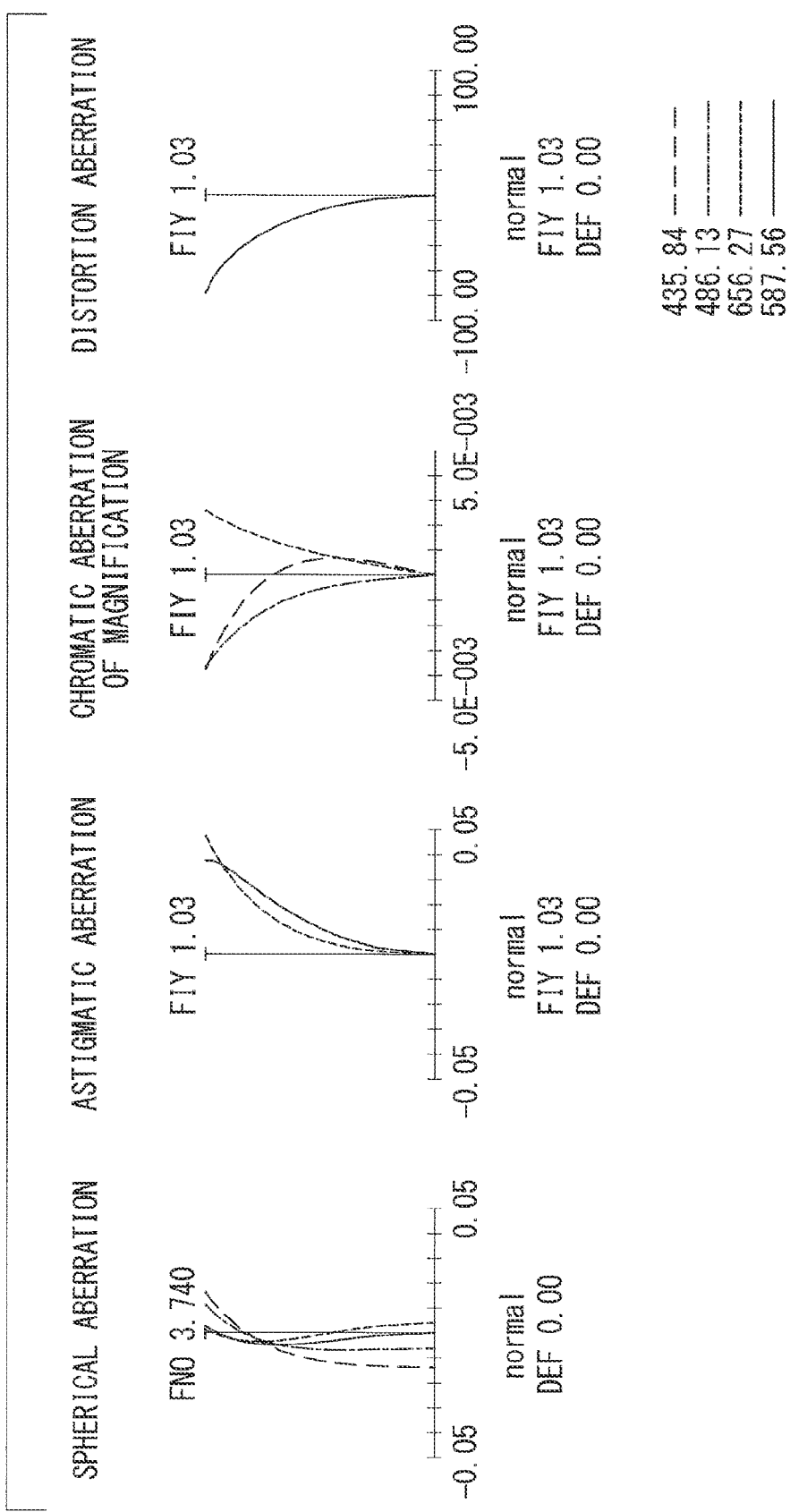
FIG. 23 is an aberration curve in the normal observation mode of the objective optical system of FIG. 22(a).
Figure 24:
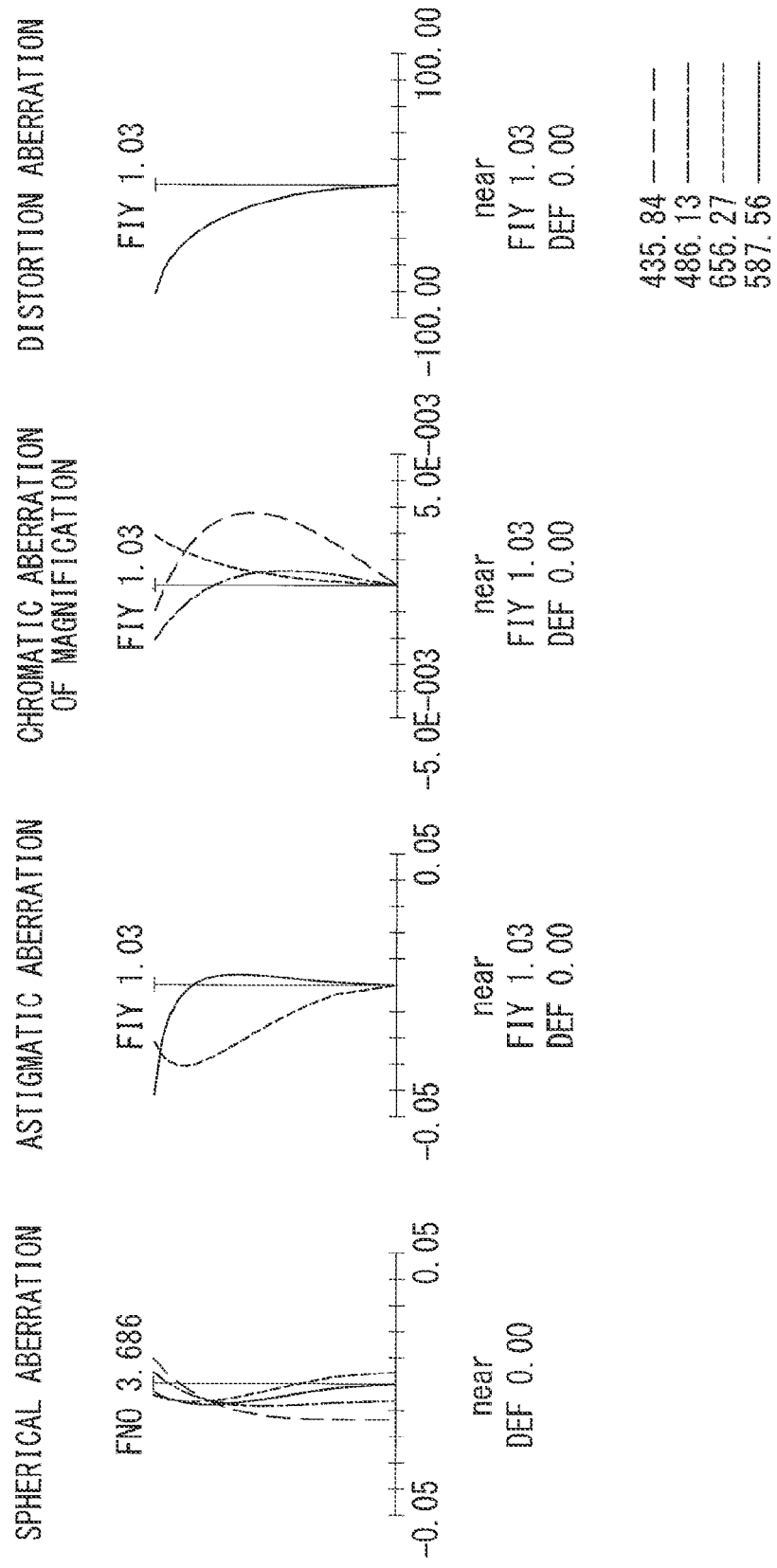
FIG. 24 is an aberration curve in the short distance observation mode of the objective optical system of FIG. 22(b).

A configuration of an endoscopic objective optical system 6 according to Example 6 of the present invention is shown in FIGS. 21 and 22. FIG. 22(a) shows a normal observation mode and FIG. 22(b) shows a short distance observation mode, and rays shown here include on-axis marginal rays and principal rays with a maximum angle of view. Also, an aberration curve in the normal observation mode of the endoscopic objective optical system 6 according to the present example is shown in FIG. 23 and an aberration curve in the short distance observation mode is shown in FIG. 24.

As shown in FIG. 22, in the endoscopic objective optical system 6 according to Example 6, the negative front group G1 includes, in order from the object side, a first lens L1 which is a plano-concave lens with a planar surface on the object side, an infrared cut filter CF, a second lens L2 which is a double-concave lens, and a third lens L3 which is a double-convex lens.

The focusing lens F is the fourth lens L4, which is a plano-concave lens with a concave surface turned to the object side, and has negative refractive power.

The positive rear group G2 includes, in order from the object side, a fifth lens L5 which is a positive meniscus lens with a convex surface turned to the image side, an aperture stop AS, a seventh lens L7 which is a plano-convex lens with a planar surface turned to the object side, an eighth lens L8 which is a double-convex lens, and a ninth lens L9 which is a negative meniscus lens with a concave surface turned to the object side. Of those lenses, the fifth lens L5 and sixth lens L6 are cemented together, forming a cemented lens CL9 and the eighth lens L8 and ninth lens L9 are cemented together, forming a cemented lens CL10.

Also, an aperture stop AS is installed between the focusing lens F and rear group G2.

During short distance observation, the fourth lens L4, which is a focusing lens F, retracts from the optical axis, setting focus to the side of shorter working distance.

Lens data of the endoscopic objective optical system 6 according to Example 6 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6561 | 1.88300 | 40.76 |
| 2 | 1.9220 | 0.7557 | 1. | |
| 3(FS) | ∞ | 0.0492 | 1. | |
| 4 | ∞ | 0.9841 | 1.51800 | 75.00 |
| 5 | ∞ | 0.1698 | 1. | |
| 6 | −5.6263 | 0.3856 | 1.88300 | 40.76 |
| 7 | 3.3960 | 0.3075 | 1. | |
| 8 | 93.7165 | 0.7666 | 1.92286 | 18.90 |
| 9 | −3.7545 | 0.7132 | 1. | |
| 10 | (r10) | 0.4920 | (GLA10) | |
| 11 | (r11) | 1.5089 | 1. | |
| 12(FS) | ∞ | 0.0492 | 1. | |
| 13 | −62.7030 | 0.8784 | 1.92286 | 18.90 |
| 14 | −2.8707 | 0.4100 | 2.00330 | 28.27 |
| 15 | 8.2363 | 0.0328 | 1. | |
| 16(AS) | ∞ | 0.0492 | 1. | |
| 17 | ∞ | 0.7784 | 1.48749 | 70.23 |
| 18 | −2.3726 | 0.0820 | 1. | |
| 19 | 3.6087 | 1.2486 | 1.48749 | 70.23 |
| 20 | −1.8711 | 0.4920 | 1.92286 | 18.90 |
| 21 | −2.9189 | 0.7786 | 1. | |
| 22(FS) | ∞ | 0.0492 | 1. | |
| 23 | ∞ | 0.0541 | 1.53000 | 56.00 |
| 24 | ∞ | 5.9176 | 1.72916 | 54.68 |
| 25 | ∞ | 0.0164 | 1.51000 | 64.00 |
| 26 | ∞ | 0.8201 | 1.61062 | 50.495 |
| 27 | ∞ | 0.3280 | 1. | |
| Image surface | ∞ | 0. | | |

| Various data | Normal observation | Short distance observation |
|---|---|---|
| d0 | 21.00000 | 4.60000 |
| r10 | −79.24365 | ∞ |
| r11 | ∞ | ∞ |
| GLA10 | 1.51633, 64.14 | Air |

Example 7

Figure 25:
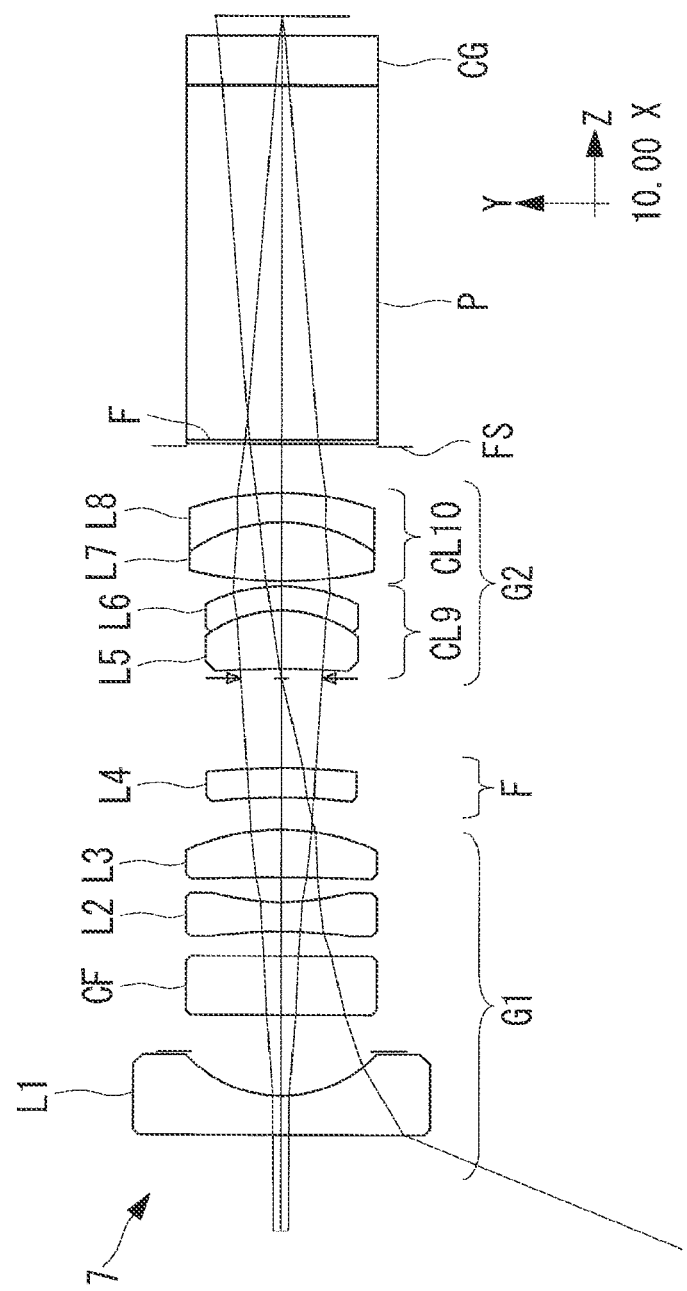
FIG. 25 is a sectional view showing an overall configuration of an objective optical system according to Example 7 of the present invention.
Figure 26:
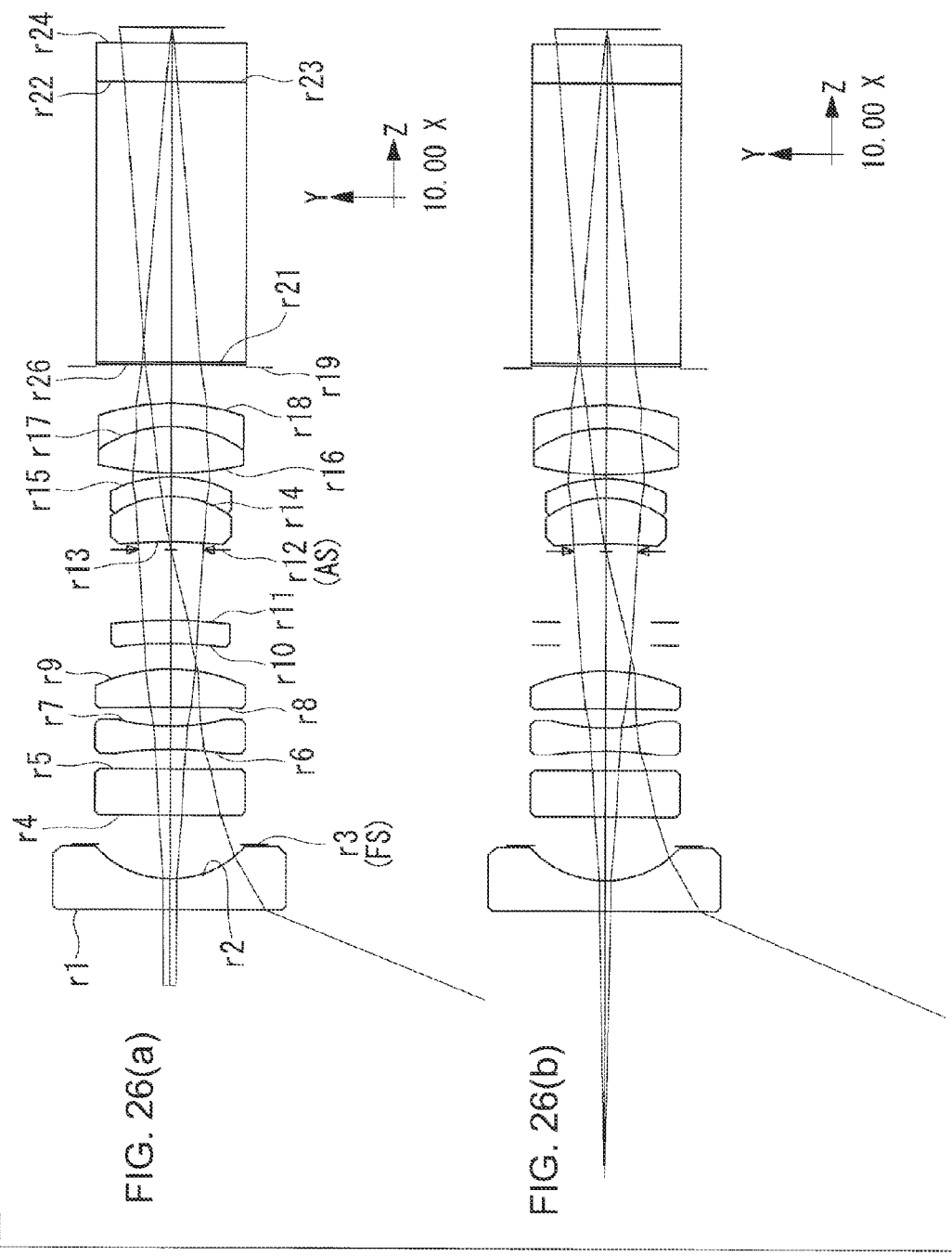
FIGS. 26(a) and 26(b) are sectional views showing the overall configuration of the objective optical system according to Example 7 of the present invention, where
Figure 27:
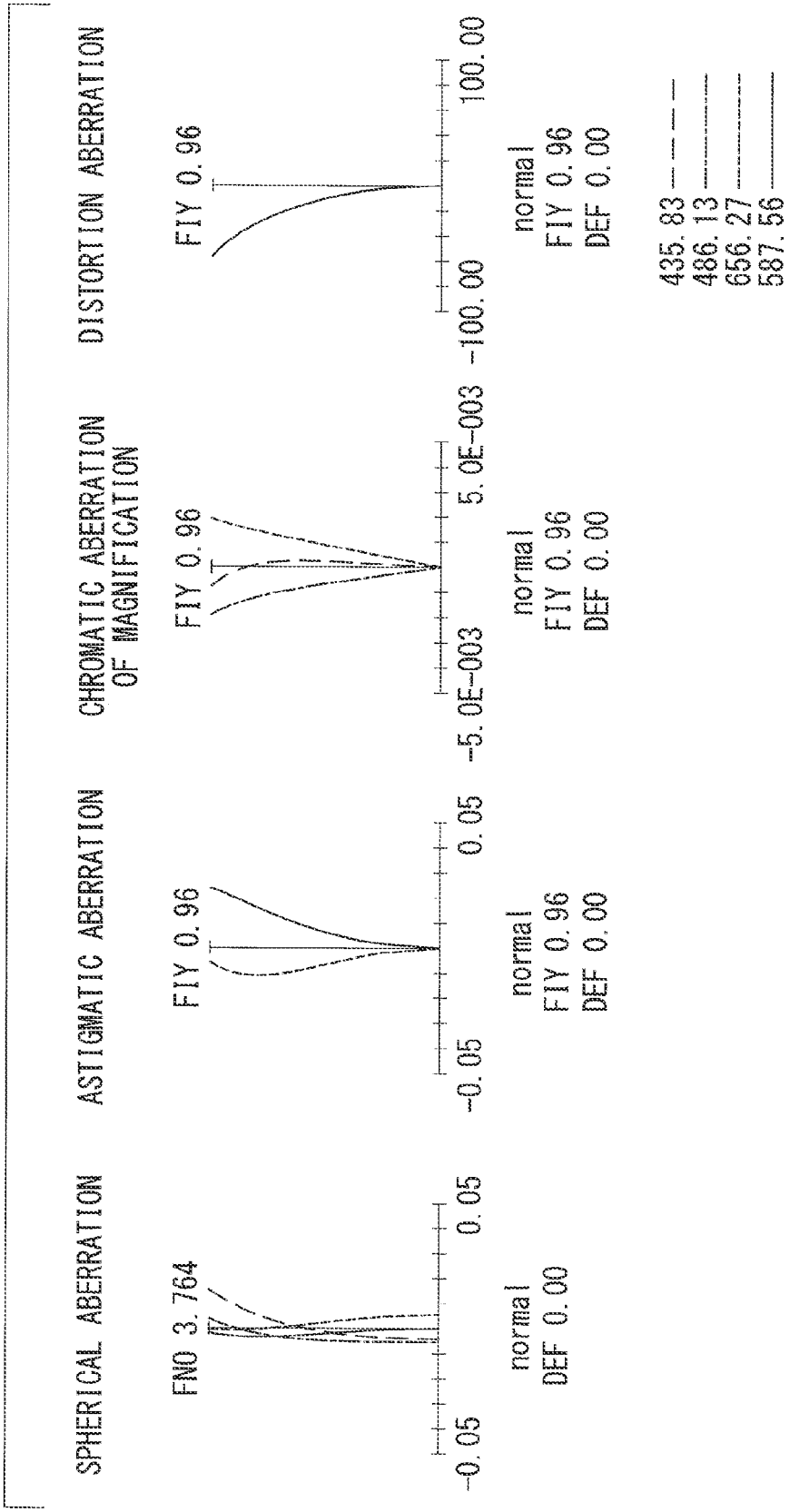
FIG. 27 is an aberration curve in the normal observation mode of the objective optical system of FIG. 26(a).
Figure 28:
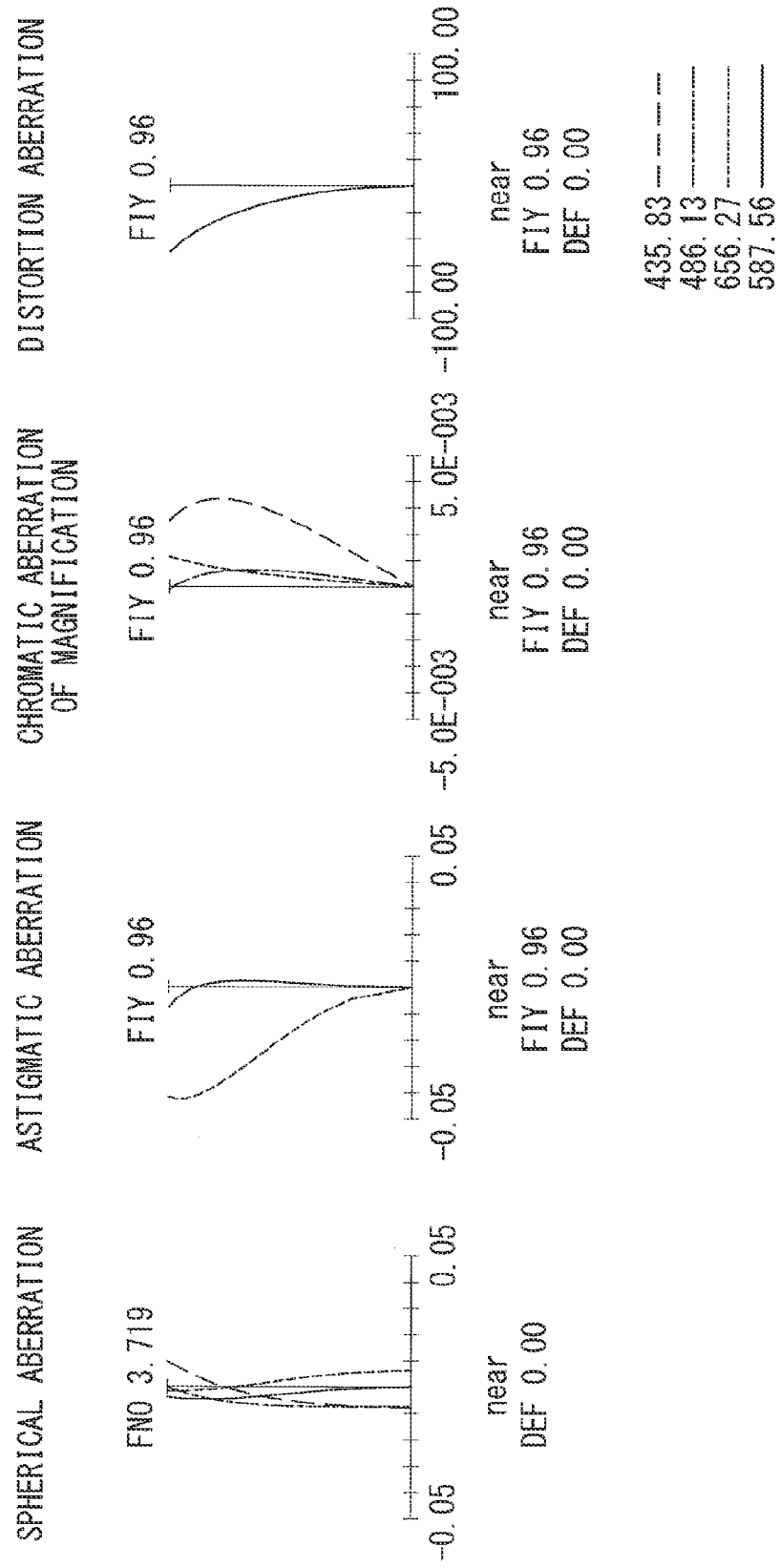
FIG. 28 is an aberration curve in the short distance observation mode of the objective optical system of FIG. 26(b).

A configuration of an endoscopic objective optical system 7 according to Example 7 of the present invention is shown in FIGS. 25 and 26. FIG. 26(a) shows a normal observation mode and FIG. 26(b) shows a short distance observation mode, and rays shown here include on-axis marginal rays and principal rays with a maximum angle of view. Also, an aberration curve in the normal observation mode of the endoscopic objective optical system 7 according to the present example is shown in FIG. 27 and an aberration curve in the short distance observation mode is shown in FIG. 28.

As shown in FIG. 25, in the endoscopic objective optical system 7 according to Example 7, the negative front group G1 includes, in order from the object side, a first lens L1 which is a plano-concave lens with a planar surface on the object side, an infrared cut filter CF, a second lens L2 which is a double-concave lens, and a third lens L3 which is a positive meniscus lens with a convex surface turned to the image side.

The focusing lens F is a fourth lens, which is a negative meniscus lens with a concave surface turned to the object side, and has negative refractive power.

The positive rear group G2 includes a fifth lens L5 which is a positive meniscus lens with a convex surface turned to the image side, a sixth lens L6 which is a negative meniscus lens with a concave surface turned to the object side, a seventh lens L7 which is a double-convex lens, and an eighth lens L8 which is a negative meniscus lens with a concave surface turned to the object side. Of those lenses, the fifth lens L5 and sixth lens L6 are cemented together, forming a cemented lens CL9 and the seventh lens L7 and eighth lens L8 are cemented together, forming a cemented lens CL10.

Also, an aperture stop AS is installed between the focusing lens F and rear group G2.

During short distance observation, the fourth lens which is a focusing lens, retracts from the optical axis, setting focus to the side of shorter working distance.

Lens data of the endoscopic objective optical system 7 according to Example 7 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6131 | 1.88300 | 40.76 |
| 2 | 1.7879 | 0.6897 | 1. | |
| 3(FS) | ∞ | 0.5749 | 1. | |
| 4 | ∞ | 0.9196 | 1.51800 | 75.00 |
| 5 | ∞ | 0.3832 | 1. | |
| 6 | −6.8635 | 0.4598 | 1.88300 | |
| 7 | 3.5076 | 0.3832 | 1. | |
| 8 | −35.3125 | 0.7510 | 1.92286 | |
| 9 | −3.0759 | 0.5044 | 1. | |
| 10 | (r10) | 0.4598 | (GLA10) | |
| 11 | (r11) | 1.4035 | 1. | |
| 12(AS) | ∞ | 0.1533 | 1. | |
| 13 | −10.8850 | 0.9043 | 1.53172 | 48.84 |
| 14 | −1.7164 | 0.3832 | 2.00330 | 28.27 |
| 15 | −2.2765 | 0.0766 | 1. | |
| 16 | 5.5291 | 0.9196 | 1.48749 | 70.23 |
| 17 | −2.1547 | 0.4598 | 1.92286 | 18.90 |
| 18 | −3.7217 | 0.7231 | 1. | |
| 19(FS) | ∞ | 0.0460 | 1. | |
| 20 | ∞ | 0.0506 | 1.53000 | 56.00 |
| 21 | ∞ | 5.5298 | 1.72916 | 54.68 |
| 22 | ∞ | 0.0153 | 1.51000 | 64.00 |
| 23 | ∞ | 0.7663 | 1.61062 | 50.49 |
| 24 | ∞ | 0.3065 | 1. | |
| Image surface | ∞ | 0. | | |

| Various data | Normal observation | Short distance observation |
|---|---|---|
| d0 | 19.20000 | 5.30000 |
| r10 | −8.11519 | ∞ |
| r11 | −9.67274 | ∞ |
| GLA10 | 1.51633, 64.14 | Air |

Example 8

Figure 29:
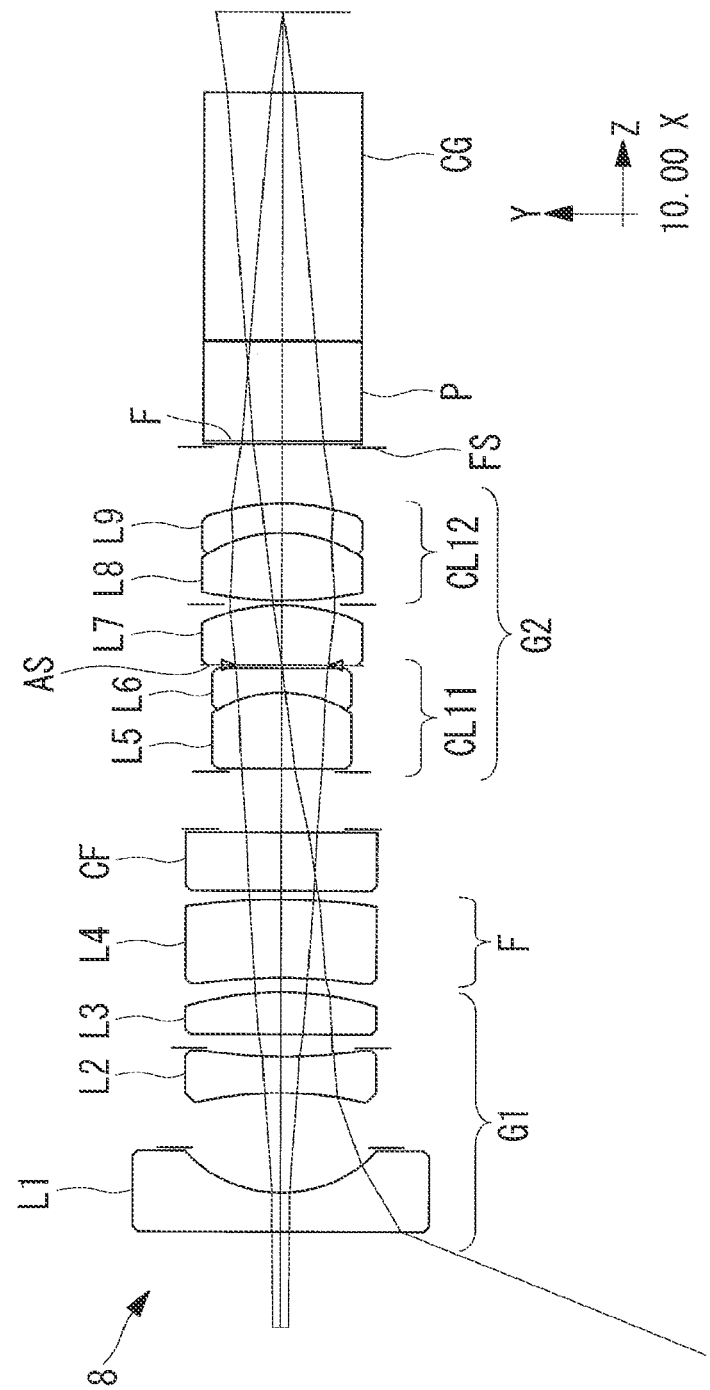
FIG. 29 is a sectional view showing an overall configuration of an objective optical system according to Example 8 of the present invention.
Figure 30:
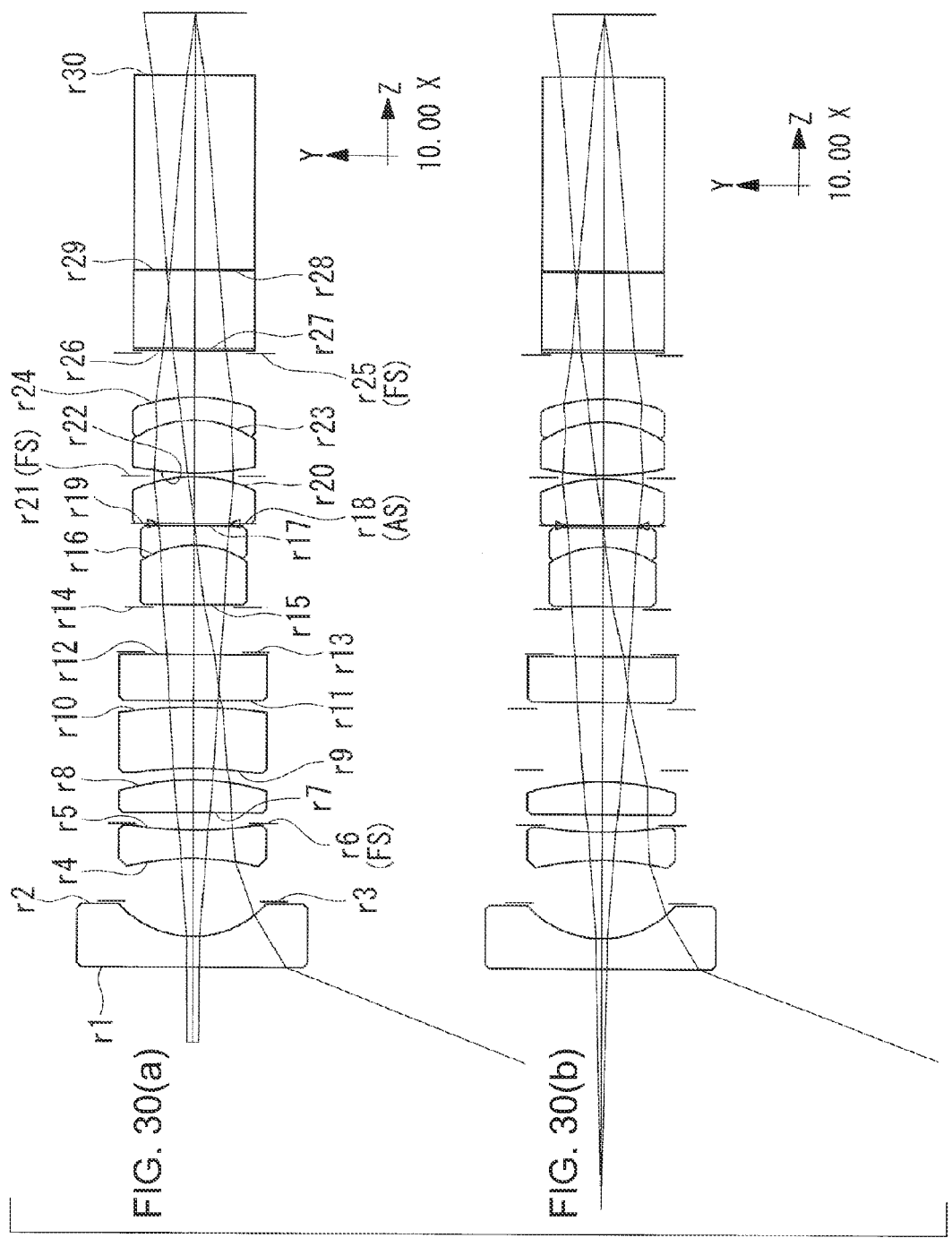
FIGS. 30(a) and 30(b) are sectional views showing the overall configuration of the objective optical system according to Example 8 of the present invention, where
Figure 31:
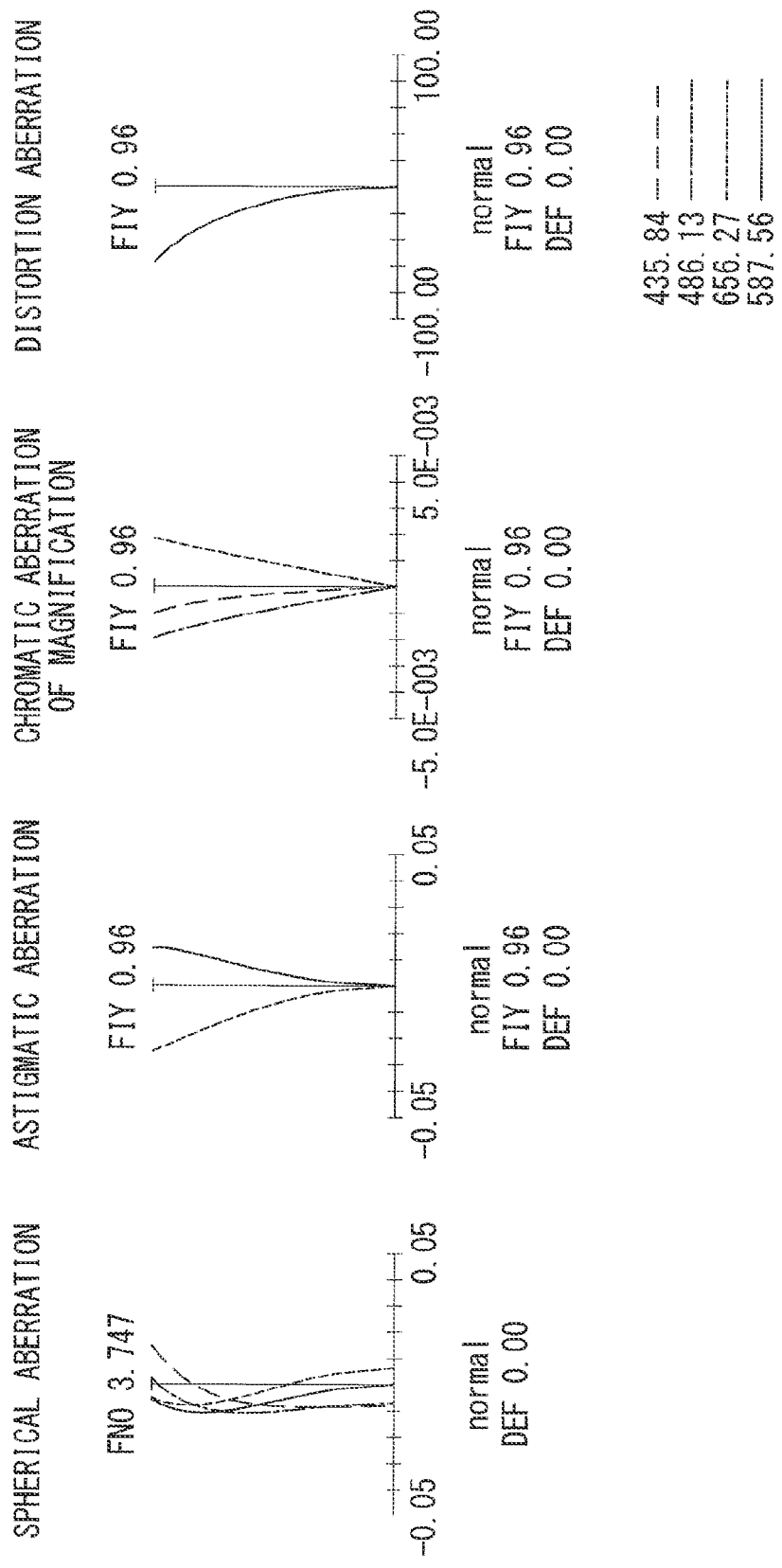
FIG. 31 is an aberration curve in the normal observation mode of the objective optical system of FIG. 30(a).
Figure 32:
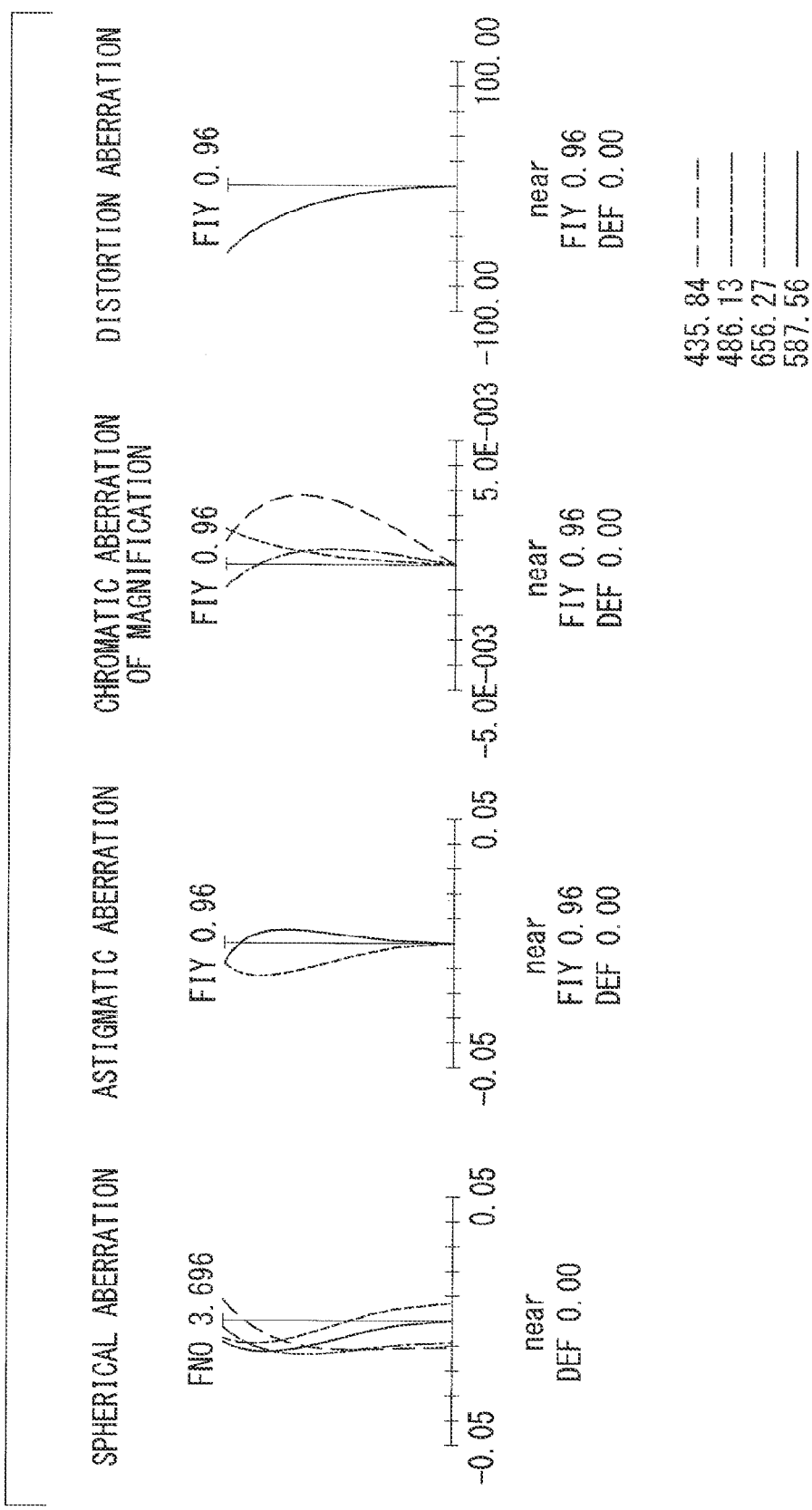
FIG. 32 is an aberration curve in the short distance observation mode of the objective optical system of FIG. 30(b).

A configuration of an endoscopic objective optical system 8 according to Example 8 of the present invention is shown in FIGS. 29 and 30. FIG. 30(a) shows a normal observation mode and FIG. 30(b) shows a short distance observation mode, and rays shown here include on-axis marginal rays and principal rays with a maximum angle of view. Also, an aberration curve in the normal observation mode of the endoscopic objective optical system according to the present example is shown in FIG. 31 and an aberration curve in the short distance observation mode is shown in FIG. 32.

As shown in FIG. 29, in the endoscopic objective optical system 8 according to Example 8, the negative front group G1 includes, in order from the object side, a first lens L1 which is a plano-concave lens with a planar surface on the object side, a second lens L2 which is a double-concave lens, and a third lens L3 which is a plano-convex lens with a planar surface turned to the object side.

The focusing lens F is a fourth lens L4, which is a negative meniscus lens with a concave surface turned to the object side, and has negative refractive power.

The positive rear group 2 includes a fifth lens L5 which is a plano-convex lens with a planar surface turned to the object side, a sixth lens L6 which is a plano-concave lens with a planar surface turned to the image side, an aperture stop AS, a seventh lens L7 which is a plano-convex lens with a planar surface turned to the object side, an eighth lens L8 which is a double-convex lens, and a ninth lens L9 which is a negative meniscus lens with a concave surface turned to the object side. Of those lenses, the fifth lens L5 and sixth lens L6 are cemented together, forming a cemented lens CL11 and the eighth lens L8 and ninth lens L9 are cemented together, forming a cemented lens CL12.

An infrared cut filter CF is installed between the focusing lens F and rear group G2.

During short distance observation, the fourth lens, which is a focusing lens, retracts from the optical axis, setting focus to the side of shorter working distance.

Lens data of the endoscopic objective optical system 8 according to Example 8 of the present invention is shown below.

| Lens data | | | | |
|---|---|---|---|---|
| Surface number | r | d | Nd | Vd |
| Object surface | ∞ | (d0) | 1. | |
| 1 | ∞ | 0.6110 | 1.88300 | 40.76 |
| 2 | 1.7735 | 0.7027 | 1. | |

-continued

| Lens data | | | | |
|---|---|---|---|---|
| 3(FS) | ∞ | 0.8554 | 1. | |
| 4 | −4.9355 | 0.5652 | 1.88300 | 40.76 |
| 5 | 6.8999 | 0.1375 | 1. | |
| 6(FS) | ∞ | 0.2139 | 1. | |
| 7 | ∞ | 0.6568 | 1.92286 | 18.90 |
| 8 | −4.3352 | 0.2291 | 1. | |
| 9 | (r9) | 1.2220 | (GLA9) | |
| 10 | (r10) | 0.1375 | 1. | |
| 11 | ∞ | 0.9165 | 1.51800 | 75.00 |
| 12 | ∞ | 0.0458 | 1. | |
| 13(FS) | ∞ | 0.9013 | 1. | |
| 14(FS) | ∞ | 0.0458 | 1. | |
| 15 | ∞ | 1.1915 | 1.69895 | 30.13 |
| 16 | −1.6925 | 0.3819 | 1.88300 | 40.76 |
| 17 | ∞ | 0.0458 | 1. | |
| 18(AS) | ∞ | 0. | 1. | |
| 19 | ∞ | 0.9318 | 1.48749 | 70.23 |
| 20 | −2.5754 | 0.0153 | 1. | |
| 21(FS) | ∞ | | 0.0611 | 1. |
| 22 | 5.2685 | 1.0540 | 1.48749 | 70.23 |
| 23 | −1.8987 | 0.4583 | 1.92286 | 18.90 |
| 24 | −2.9955 | 0.8821 | 1. | |
| 25(FS) | ∞ | | 0.0458 | 1. |
| 26 | ∞ | 0.0504 | 1.53000 | 56.00 |
| 27 | ∞ | 1.5489 | 1.72916 | 54.68 |
| 28 | ∞ | 0.0215 | 1.51000 | 64.00 |
| 29 | ∞ | 3.8647 | 1.72916 | 54.68 |
| 30 | ∞ | 1.2474 | 1. | |
| Image surface | ∞ | 0. | | |

| Various data | Normal observation | Short distance observation |
|---|---|---|
| d0 | 19.70000 | 4.80000 |
| r9 | −7.28027 | ∞ |
| r10 | −9.26913 | ∞ |
| GLA9 | 1.88300, 40.76 | Air |

Numerical values of above-mentioned conditional expressions (1) to (4) in the configurations of Examples 1 to 8 described above are shown in Table 1.

TABLE 1

| CONDITIONAL EXPRESSION No. | EXPRESSION | EXAMPLE 1 | EXAMPLE 2 | EXAMPLE 3 | EXAMPLE 4 | EXAMPLE 5 | EXAMPLE 6 | EXAMPLE 7 | EXAMPLE 8 | LOWER LIMIT | UPPER LIMIT |
|---|---|---|---|---|---|---|---|---|---|---|---|
| 1 | FB/FL | 4.893 | 4.654 | 4.666 | 4.623 | 4.664 | 5.089 | 4.744 | 5.306 | 4.000 | — |
| 2 | FL/|fc| | 0.056 | 0.059 | 0.021 | 0.051 | 0.054 | 0.007 | 0.009 | 0.019 | — | 0.100 |
| 3 | F_F/FL | −1.110 | −1.050 | −1.793 | −2.392 | −1.980 | −1.897 | −2.454 | −2.059 | −3.000 | −0.900 |
| 4 | F_R/FL | 3.803 | 3.566 | 3.991 | 3.387 | 3.310 | 3.436 | 3.516 | 3.635 | 2.500 | 5.000 |

TABLE 2

| | | EXAMPLE 1 | EXAMPLE 2 | EXAMPLE 3 | EXAMPLE 4 | EXAMPLE 5 | EXAMPLE 6 | EXAMPLE 7 | EXAMPLE 8 |
|---|---|---|---|---|---|---|---|---|---|
| | MODE | NORMAL | | | | | | | |
| WORKING DISTANCE | WD | 20.4 | 19.4 | 19.4 | 19.2 | 19.4 | 21 | 19.2 | 19.7 |
| FOCAL LENGTH OF ENTIRE SYSTEM | FL | 1.000 | 1.000 | 1.000 | 1.000 | 1.000 | 1.000 | 1.000 | 1.000 |
| EFFECTIVE F-no. | EFFECTIVE F-no. | 3.755 | 3.754 | 3.758 | 3.739 | 3.735 | 3.762 | 3.787 | 3.769 |
| ANGLE OF VIEW(deg.) | 2ω | 159.3 | 138.1 | 136.8 | 133.3 | 133.3 | 157.3 | 132.6 | 133.5 |
| IMAGE HEIGHT | IH | 0.989 | 0.942 | 0.944 | 0.934 | 0.942 | 1.027 | 0.959 | 0.956 |
| BACK FOCUS OF ENTIRE OBJECTIVE LENS SYSTEM (DURING NORMAL OBSERVATION) | FB | 4.893 | 4.654 | 4.666 | 4.623 | 4.664 | 5.089 | 4.744 | 5.306 |
| FOCAL LENGTH OF FOCUS LENS | fc | 17.798 | 16.907 | 48.454 | −19.493 | −18.411 | −153.475 | −108.515 | −53.979 |

TABLE 2-continued

| | | EXAMPLE 1 | EXAMPLE 2 | EXAMPLE 3 | EXAMPLE 4 | EXAMPLE 5 | EXAMPLE 6 | EXAMPLE 7 | EXAMPLE 8 |
|---|---|---|---|---|---|---|---|---|---|
| FOCAL LENGTH OF FRONT GROUP | F_F | −1.110 | −1.050 | −1.793 | −2.392 | −1.980 | −1.897 | −2.454 | −2.059 |
| FOCAL LENGTH OF REAR GROUP | F_R | 3.803 | 3.566 | 3.991 | 3.387 | 3.310 | 3.436 | 3.516 | 3.635 |

TABLE 3

| | | EXAMPLE 1 | EXAMPLE 2 | EXAMPLE 3 | EXAMPLE 4 | EXAMPLE 5 | EXAMPLE 6 | EXAMPLE 7 | EXAMPLE 8 |
|---|---|---|---|---|---|---|---|---|---|
| MODE | | NEAR | | | | | | | |
| WPRKING DISTANCE | WD | 4.9 | 4.7 | 4.7 | 4.6 | 4.6 | 4.6 | 5.3 | 4.8 |
| FOCAL LENGTH OF ENTIRE SYSTEM | FL | 0.999 | 1.002 | 0.996 | 0.990 | 0.984 | 0.978 | 0.997 | 0.989 |
| EFFECTIVE F-no. | EFFECTIVE F-no. | 3.760 | 3.760 | 3.760 | 3.736 | 3.730 | 3.761 | 3.790 | 3.771 |
| ANGLE OF VIEW(deg.) | 2ω | 150.7 | 132.3 | 132.3 | 136.3 | 136.6 | 164.6 | 130.5 | 135.3 |
| IMAGE HEIGHT | IH | | | | | | | | |
| BACK FOCUS OF ENTIRE OBJECTIVE LENS SYSTEM (DURING NORMAL OBSERVATION) | FB | | | | | | | | |
| FOCAL LENGTH OF FOCUS LENS | fc | | | | | | | | |
| FOCAL LENGTH OF FRONT GROUP | F_F | | | | | | | | |
| FOCAL LENGTH OF REAR GROUP | F_R | | | | | | | | |

Second Embodiment

Next, a second embodiment of the present invention will be described.

The endoscopic objective optical system according to each of the examples described above can be applied to an imaging apparatus and an example of an imaging apparatus resulting from application of any of the above-mentioned endoscopic objective optical systems (hereinafter referred to simply as "objective optical systems") will be described below.

FIGS. 33(a) and 33(b) show a schematic configuration of an imaging apparatus 10 according to the second embodiment of the present invention, where FIG. 33(a) is diagram schematically showing an overall configuration and FIG. 33(b) is diagram showing orientations of subjects in images formed, respectively, in a first and second regions of an imaging device.

Figure 33:
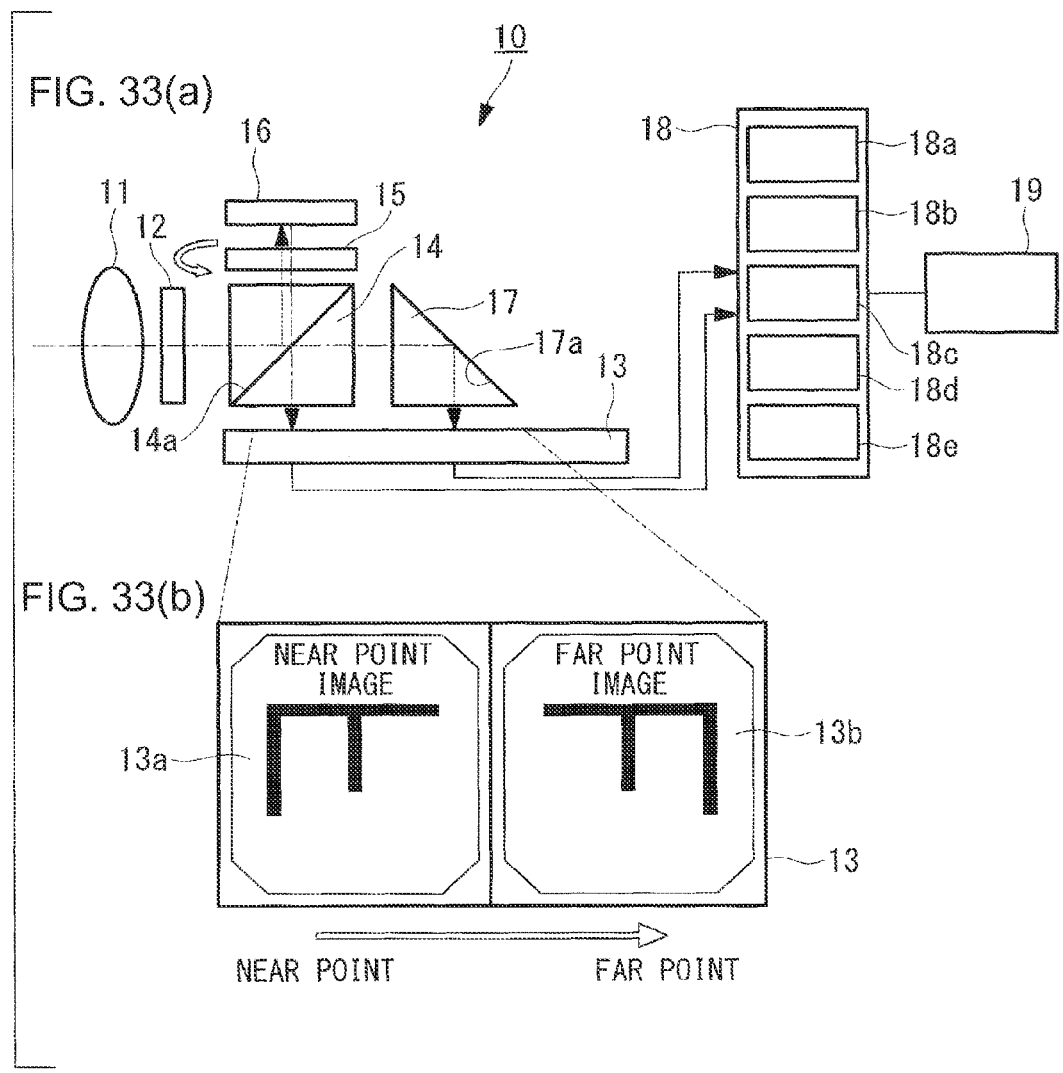
FIGS. 33(a) and 33(b) are explanatory diagrams showing a schematic configuration of an imaging apparatus according to a second embodiment of the present invention, where
Figure 34:
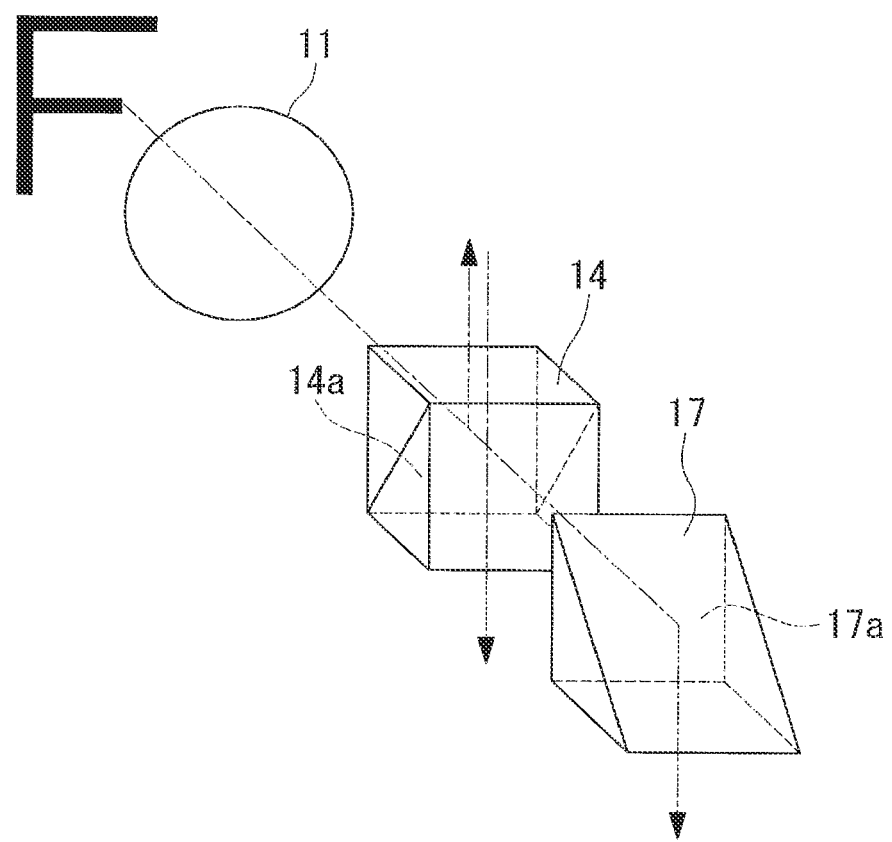
FIG. 34 is a perspective view of an objective optical system, splitting element, and second reflecting member in the imaging apparatus of FIG. 33.
Figure 35A:
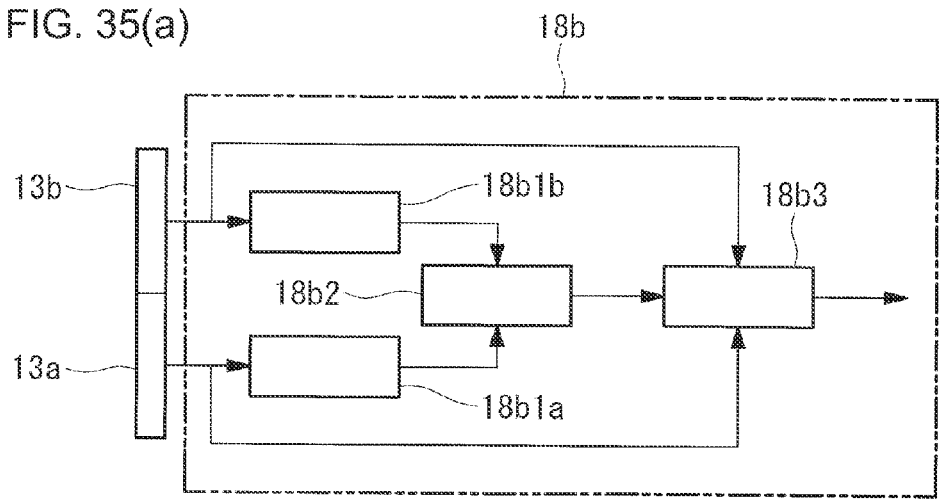
FIGS. 35(a) and 35(b) are explanatory diagrams showing configuration examples of an image selection unit in the imaging apparatus of FIG. 33, where
Figure 35B:
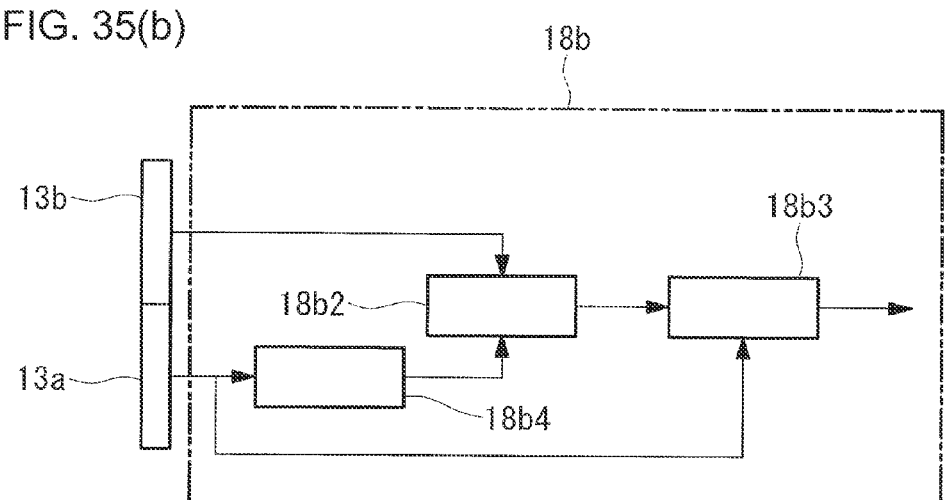

FIG. 34 is a perspective view of an objective optical system, splitting element, and second reflecting member in the imaging apparatus 10 of FIG. 33. FIGS. 35(a) and 35(b) are explanatory diagrams showing configuration examples of an image selection unit in the imaging apparatus 10 of FIG. 33, where FIG. 35(a) shows an example and FIG. 35(b) shows another example.

The imaging apparatus 10 includes the objective optical system 11 described above, a depolarizing plate 12, an imaging device 13, a polarizing beam splitter 14, a wave plate 15, a first reflecting member 16, a second reflecting member 17, and an image processing unit 18. In FIG. 33, reference numeral 19 denotes an image display device.

The objective optical system 11 has a function to focus a luminous flux from an object and the object side is configured to be telecentric. The depolarizing plate 12 is placed between the objective optical system 11 and the polarizing beam splitter 14. The imaging device 13 is made up of a CMOS sensor of a rolling shutter type and placed near an image location of the objective optical system 11.

The polarizing beam splitter 14 is located above a first region 13a of the imaging device 13 on the optical path between the objective optical system 11 and imaging device 13 and adapted to split a luminous flux from the objective optical system 11 into two luminous fluxes, i.e., a reflected luminous flux and transmitted luminous flux using a polarizing beam splitter surface 14a. Note that it is assumed here that the polarizing beam splitter 14 reflects linearly-polarized light of an s-polarized component and transmits linearly-polarized light of a p-polarized component.

The wave plate 15 is made up of a quarter-wave plate and configured to be rotatable around the optical axis. The first reflecting member 16 is made up of a mirror and configured to reflect back a luminous flux reflected off the polarizing beam splitter surface 14a and transmitted through the wave plate 15.

The second reflecting member 17 is made up of a prism and configured to reflect light transmitted through the polarizing beam splitter 14, by using a total reflection surface 17a. Note that the total reflection surface 17a may be configured by applying a mirror coating to a surface of the prism 17.

The imaging apparatus 10 according to the present embodiment focuses a luminous flux reflected off the first reflecting member 16 via the wave plate 15 and polarizing beam splitter 14 onto the first region 13a of the imaging device 13. On the other hand, the imaging apparatus 10 focuses a luminous flux reflected off the second reflecting member 17 onto a second region 13b of the imaging device 13, different from the first region 13a.

The image processing unit 18, which is connected to the imaging device 13 and installed on a central processing unit (not shown), includes a first image processing unit 18a, a second image processing unit 18b, a third image processing unit 18c, a fourth image processing unit 18d, and a fifth image processing unit 18e.

The first image processing unit 18a is configured to correct orientations (rotations) of images in the first region 13a and second region 13b.

When, a letter "F" such as shown in FIG. 34 is observed, the images formed on the first region 13a and second region 13b, respectively, are orientated as shown in FIG. 33 (B). That is, the image formed on the first region 13a rotates 90 degrees clockwise around a center point of the first region 13a and assumes an orientation rotated 180 degrees around a vertical axis in FIG. 33 (B) passing through the center point of the first region 13a. Also, the image formed on the second region 13b assumes an orientation rotated 90 degrees clockwise around a center point of the second region 13b.

Thus, when the images formed, respectively, on the first region 13a and second region 13b are displayed on the image display device 19, the images formed, respectively, on the first region 13a and second region 13b are rotated 90 degrees counterclockwise around the center points of the respective regions via the first image processing unit 18a, and moreover, the image in the first region 13a is rotated 180 degrees around the vertical axis in FIG. 33 (B) passing through the center point of the first region 13a, to correct a mirror image.

The third image processing unit 18c is configured to be able to adjust respective white balances of the first region 13a and second region 13b.

The fourth image processing unit 18d is configured to be able to move (select) respective center positions of the images in the first region 13a and second region 13b.

The fifth image processing unit 18e is configured to be able to adjust respective display ranges (magnifications) of the images in the first region 13a and second region 13b.

The second image processing unit 18b, which corresponds to an image selection unit according to the present invention, is configured to compare the image in the first region 13a and image in the second region 13b and select the image in the region in focus as an image for display.

Specifically, for example, as shown in FIG. 35a, the second image processing unit 18b includes high-pass filters 18b1a and 18b1b connected to the respective regions 13a and 13b, a comparator 18b2 connected to the high-pass filters 18b1a and 18b1b, and a switch 18b3 connected to the comparator 18b2 and each of the regions 13a and 13b. The second image processing unit 18b is configured to extract high frequency components from the images in the first region 13a and second region 13b using the high-pass filters 18b1a and 18b1b, compare the extracted high frequency components using the comparator 18b2, and select the image in the region with a larger volume of high frequency components using the switch 18b3.

Alternatively, for example, as shown in FIG. 35 (B), the second image processing unit 18b may include, a defocus filter 18b4 connected to only the first region 13a, a comparator 18b2 connected to the defocus filter 18b4 as well as to the second region 13b, a switch 18b3 connected to the first region 13a and comparator 18b2, and may be configured to compare an image signal of the first region 13a defocused by the defocus filter 18b4 and an image signal of the non-defocused second region 13b using the comparator 18b2 and select the image in the second region 13b in a portion where the image signals match and select the image in the region 13a in a portion where the image signals do not match, by using the switch 18b3.

The image display device 19 includes a display area adapted to display an image selected by the second image processing unit 18b. Note that the image display device 19 may include display areas adapted to display images formed on the first and second regions 13a and 13b, respectively.

In the imaging apparatus 10 configured in this way, the luminous flux from the objective optical system 11 has a deviation in a polarization direction cancelled out by passing through the depolarizing plate 12 and enters the polarizing beam splitter 14. Upon entering the polarizing beam splitter 14, the light is separated into an s-polarized component and p-polarized component of linearly-polarized light by the polarizing beam splitter surface 14a.

A luminous flux of the linearly-polarized light of the s-polarized component reflected off the polarizing beam splitter surface 14a is converted into circularly-polarized light in terms of polarization state by passing through the quarter-wave plate 15 and is then reflected off the mirror 16. The luminous flux reflected off the mirror 16 passes through the quarter-wave plate 15 again, has its polarization state converted from circularly-polarized light into linearly-polarized light of an p-polarized component, and enters the polarizing beam splitter 14 again. Then, the luminous flux is transmitted through the polarizing beam splitter surface 14a and focused on the first region 13a of the imaging device 13.

Also, after passing the objective optical system 11 and depolarizing plate 12, the luminous flux of the linearly-polarized light of the s-polarized component is transmitted through the polarizing beam splitter surface 14a when entering the polarizing beam splitter 14, reflected off the total reflection surface 17a of the prism 17, and focused on the second region 13b of the imaging device 13.

The imaging device 13, which is configured to be a rolling shutter type as described above, reads an image line by line in the direction indicated by an arrow in FIG. 33(b). The second image processing unit 18b compares the images read line by line and formed on the first region 13a and second region 13b, respectively, and selects the image in focus as an image for display.

Note that the lines of the image selected by the second image processing unit 18b are composed and displayed on the image display device 19.

The embodiments described above are derived from aspects of the present invention presented below.

That is, one aspect of the present invention provides an endoscopic objective optical system comprising, in order from an object side to an image side, a front group provided with negative refractive power, a focusing lens, and a rear group provided with positive refractive power, wherein: the front group and the rear group are always fixed on an optical axis; and the endoscopic objective optical system satisfies conditional expressions (1) to (4) below:

$$4 < FB/FL \quad (1)$$

$$FL/|fc| < 0.1 \quad (2)$$

$$-3 < F\_F/FL < -0.9 \quad (3)$$

$$2.5 < F\_R/FL < 5 \quad (4)$$

where FB is back focus of the entire endoscopic objective optical system, the back focus being a distance from a lens surface of the rear group closest to the image side to a back focus position of the entire system, FL is a focal length of the entire endoscopic objective optical system, fc is a focal length of the focusing lens, |fc| is an absolute value of fc, F_F is a focal length of the front group, and F_R is a focal length of the rear group.

By satisfying the above conditional expressions, the present aspect reduces variations in aberrations due to manufacturing errors and variations in aberrations due to focusing by prescribing the focal length of the focusing lens while allowing placement of optical members such as a polarizing prism. Specifically, the present aspect makes it possible to suppress aberrations due to manufacturing errors, decrease influence on deterioration of optical performance, and, for example, reduce side blur. Also, the present aspect makes it possible to suppress variations in aberrations due to focusing, decrease variations in astigmatic aberrations, and prevent an image surface from becoming liable to incline to a negative side on a side of shorter working distance. Note that the focusing lens has positive or negative weak refractive power.

Also, the present aspect makes it possible to decrease influence of eccentricity errors on deterioration of optical performance while maintaining sufficient refractive power of the front group so as to be advantageous for a wider angle of view and reducing high order off-axis aberrations.

Furthermore, the present aspect makes it possible to keep lens size in a desired range while maintaining refractive power of the rear group and ensuring back focus.

In the aspect described above, preferably the focusing lens has positive refractive power; and focus is set to a side of shorter working distance by moving the focusing lens to an image side when the working distance changes from a longer side to the shorter side.

This makes it possible to set focus to the side of shorter working distance by moving the focusing lens to the image side on the optical axis.

In the aspect described above, preferably the focusing lens has negative refractive power; and focus is set to a side of shorter working distance by moving the focusing lens to an object side when the working distance changes from a longer side to the shorter side.

This makes it possible to set focus to the side of shorter working distance by moving the focusing lens to the object side on the optical axis.

Also, another aspect of the present invention provides an imaging apparatus comprising: the endoscopic objective optical system; one imaging device placed in a neighborhood of an image location of the endoscopic objective optical system; a splitting element placed between the objective lens and the imaging device and adapted to split a luminous flux from the objective lens into two luminous fluxes, that is, a reflected luminous flux and transmitted luminous flux; a first reflecting member adapted to reflect back the reflected luminous flux; and a second reflecting member adapted to reflect the transmitted luminous flux, wherein the luminous flux reflected by the first reflecting member via the splitting element is focused on a first region of the imaging device, and the luminous flux reflected by the second reflecting member is focused on a second region of the imaging device, different from the first region.

The endoscopic objective optical system described above has a long back focus, allows placement of optical members, makes aberrations less subject to manufacturing errors, reduces variations in aberrations during focusing, and thus makes it possible to acquire high-quality subject images when applied to an imaging apparatus.

Advantageous Effects of Invention

The present invention offers the effects of allowing placement of optical members such as a polarizing prism due to a long back focus, making aberrations less subject to manufacturing errors, and reducing variations in aberrations during focusing.

REFERENCE SIGNS LIST

1 to 8 Endoscopic objective optical system
10 Imaging apparatus
11 Objective optical system
12 Depolarizing plate
13 Imaging device
14 Polarizing beam splitter
15 Wave plate
16 First reflecting member
17 Second reflecting member
18 Image processing unit
19 Image display device
G1 Front group
G2 Rear group
L1 First lens
L2 Second lens
L3 Third lens
L4 Fourth lens
L5 Fifth lens
L6 Sixth lens
L7 Seventh lens
L8 Eighth lens
L9 Ninth lens
L10 Tenth lens
CL1 to CL12 Cemented lens
AS Aperture stop
FS Flare stop
P Optical prism
CG Cover glass

The invention claimed is:

1. An endoscopic objective optical system comprising, in order from an object side to an image side, a front group provided with at least one first cemented lens having negative refractive power, a focusing lens provided with a second cemented lens or a single lens, and a rear group provided with positive refractive power, wherein:

the front group and the rear group are always fixed on an optical axis; the focusing lens is provided to be moved along an optical axis; and the endoscopic objective optical system satisfies conditional expressions (1) to (4) below:

$$4 < FB/FL \tag{1}$$

$$FL/|fc| < 0.1 \tag{2}$$

$$-3 < F\_F/FL < -0.9 \tag{3}$$

$$2.5 < F\_R/FL < 5 \tag{4}$$

where FB is back focus of the entire endoscopic objective optical system, the back focus being a distance from a lens surface of the rear group closest to the image side to a back focus position of the entire system, FL is a focal length of the entire endoscopic objective optical system, fc is a focal length of the focusing lens, |fc| is an absolute value of fc, F_F is a focal length of the front group, and F_R is a focal length of the rear group.

2. The endoscopic objective optical system according to claim 1, wherein:

the focusing lens has positive refractive power; and focus is set to a side of shorter working distance by moving the focusing lens to an image side when the working distance changes from a longer side to the shorter side.

3. The endoscopic objective optical system according to claim 1, wherein:

the focusing lens has negative refractive power; and focus is set to a side of shorter working distance by moving the focusing lens to an object side when the working distance changes from a longer side to the shorter side.

4. An imaging apparatus comprising:

the endoscopic objective optical system according to claim 1;

one imaging device placed in a neighborhood of an image location of the endoscopic objective optical system;

a splitting element placed between the objective lens and the imaging device and adapted to split a luminous flux from the objective lens into two luminous fluxes, that is, a reflected luminous flux and transmitted luminous flux;

a first reflecting member adapted to reflect back the reflected luminous flux; and a second reflecting member adapted to reflect the transmitted luminous flux, wherein the luminous flux reflected by the first reflecting member via the splitting element is focused on a first region of the imaging device, and the luminous flux reflected by the second reflecting member is focused on a second region of the imaging device, different from the first region.

* * * * *